US009029143B2

(12) United States Patent
Goletz et al.

(10) Patent No.: US 9,029,143 B2
(45) Date of Patent: May 12, 2015

(54) MUTZ-3 DENDRITIC CELLS

(75) Inventors: Steffen Goletz, Glienicke (DE); Rik J. Scheper, Amsterdam (NL); Alan Masterson, Amsterdam (NL); Herbert M. Pinedo, Amsterdam (NL)

(73) Assignee: Glycotope GmbH, Berlin (DE)

( * ) Notice: Subject to any disclaimer, the term of this patent is extended or adjusted under 35 U.S.C. 154(b) by 0 days.

(21) Appl. No.: 13/553,157

(22) Filed: Jul. 19, 2012

(65) Prior Publication Data

US 2012/0308607 A1 Dec. 6, 2012

Related U.S. Application Data

(62) Division of application No. 10/486,966, filed as application No. PCT/EP02/09260 on Aug. 19, 2002, now Pat. No. 8,455,253.

(30) Foreign Application Priority Data

Aug. 17, 2001 (DE) .................................. 101 39 428

(51) Int. Cl.
*C12N 5/09* (2010.01)
*A61K 39/00* (2006.01)
*C12N 5/0784* (2010.01)

(52) U.S. Cl.
CPC .......... *C12N 5/0694* (2013.01); *A61K 39/0011* (2013.01); *A61K 2039/5152* (2013.01); *A61K 2039/5154* (2013.01); *A61K 2039/5156* (2013.01); *C12N 5/0639* (2013.01); *C12N 2501/15* (2013.01); *C12N 2501/22* (2013.01); *C12N 2501/24* (2013.01); *C12N 2501/25* (2013.01); *C12N 2501/39* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,648,219 A | 7/1997 | MacKay et al. | |
| 5,811,297 A | 9/1998 | Gopal | |
| 5,962,288 A | 10/1999 | Aksenov et al. | |
| 6,300,090 B1 * | 10/2001 | Steinman et al. | 435/7.24 |
| 2001/0039052 A1 | 11/2001 | Zander | |
| 2002/0041868 A1 | 4/2002 | Nicolette et al. | |
| 2002/0090381 A1 * | 7/2002 | Bottomly et al. | 424/198.1 |

FOREIGN PATENT DOCUMENTS

DE 10139428 8/2001
WO WO 9846785 A1 * 10/1998

OTHER PUBLICATIONS

Declaration of Dr. Tanja Denise de Gruijl filed in European Application No. EP02758474.7 on Mar. 19, 2012, printed as pp. 1/19-19/19.*
Declaration of Dr. Allan J. Masterson filed in European Application No. EP02758474.7 on Mar. 19, 2012, printed as pp. 1/8-8/8.*

Larsson et al. Functional and transcriptional profiling of MUTZ-3, a myeloid cell line acting as a model for dendritic cells. Immunology, vol. 117, pp. 156-166, 2006.*
Manome et al. Simple chemicals can induce maturation and apoptosis of dendritic cells. Immunology, vol. 98, pp. 481-490, 1999.*
van der Vliet et al. Potent expansion of human natural killer T cells using alpha-galactosylceramide (KRN7000)-loaded monocyte-derived dendritic cells, cultured in the presence of IL-7 and IL-15. Journal of Immunological Methods, vol. 247, pp. 61-72, Jan. 2001.*
Dietz et al. Optimizing preparation of normal dendritic cells and bcr-abl+ matur edendritic cells derived from immunomagnetically purified CD14+ cells. Journal of Hematotherapy & Stem Cell Research, vol. 9, pp. 95-101, 2000.*
Waclavicek et al. Calcium ionophore: a single reagent for the differentiation of primary human acute myelogenous leukaemia cells towards dendritic cells. British Journal of Haematology, vol. 114, pp. 466-473, Aug. 2001.*
Bernhard et al. Generation and immunostimulatory dendritic cells from human CD34+ hematopietic progenitor cells of the bone marrow and peripheral blood. Cancer Research, vol. 55, pp. 1099-1104, 1995.*
Mohty et al. Circulating blood dendritic cells from myeloid leukemia patients display quantitative and cytogenetic abnormalities as well as functional impairment. Blood, vol. 98, No. 13, pp. 3750-3756, Dec. 2001.*
Wieder. Dendritic Cells: A Basic Review. International Society for Cellular Therapy, last updated May 2003, printed from http://celltherapysociety.org as p. 1/6-6/6.*
Rasaiyaah et al. Transcriptional and functional defects of dendritic cells derived from the MUTZ-3 leukaemia line. Immunology, vol. 127, pp. 429-441, 2008.*
European Search Report for EP Appl. No. 10185184.8, European Patent Office, Issued Jul. 13, 2012.
Hu, Z-B et al., "Establishment and characterization of two novel cytokine-responsive acute myeloid and monocytic leukemia cell lines, MUTZ-2 and MUTZ-3," Leukemia, 10:6, pp. 1025-1040, 1996.
Van Helden, S. F.G et al., "Human and murine model cell lines for dendritic cell biology evaluated," Immunology Letters, 117:2, pp. 191-197, 2008.
Santegoets, S. et al., "In vitro priming of tumor-specific cytotoxic T lymphocytes using allogenic dendritic cells derived from human MUTZ-3 cell line," Cancer Immunology Immunother, 55, pp. 1480-1490, 2006.
Di Noto R. et al., "JURI-MK1 (c-kit$^{high}$/CD30$^-$/CD$^-$40) and JURL-MK2 (c-kit$^{low}$/CD30$^+$/CD40$^+$) cell lines: 'two-dided' model for investigating leukemic magakaryocytopoiesis," Leukemia, 11, pp. 1554-1564, 1997.

(Continued)

*Primary Examiner* — Jennifer Dunston
(74) *Attorney, Agent, or Firm* — Fanelli Haag PLLC

(57) ABSTRACT

The invention is related to the production and use of CD124+ and CD116+ cell lines for the production of effective dendritic cells (DC) using stimulatory molecules, their use in the production of allogenic or semi-allogenic immunotherapeutic agents and the use thereof in the treatment or prophylaxis of immune diseases. Furthermore, the invention is related to the use of CD124+ and CD116+ tumor cell lines, preferably also being CD34+, as model and test systems for testing the DC biology and for testing substances having an impact on the immune system and on the conditioning thereof.

12 Claims, 12 Drawing Sheets

(56) References Cited

OTHER PUBLICATIONS

Figure 1:
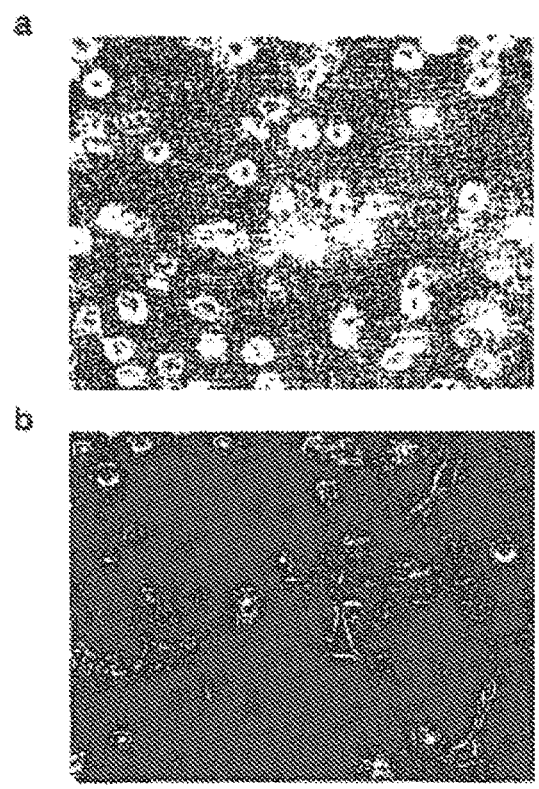

Menetreir-Caux, C. et al., "Inhibition of the Differentiation of Dendritic Cells From CD34+ Progenitors by Tumor Cells: Role of Interleukin-6 and Macrophage Colony-Stimulating Factor," Blood, 92:12, pp. 4778-4791, 1998.
Caput, D. et al., "Cloning and Characterization of a Specific Interleukin (IL)-13 Binding Protein Structurally Related to the IL-5 Receptor a Chain," 271:28, pp. 16921-16926, 1996.
Agis, H. et al., "Comparative immunophenotypic analysis of human mast cells, blood basophils and moncytes," Immunology, 87, pp. 553-543, 1996.
Liu, W.M., et al., "Effect of haemopoietic growth factors on cancer cell lines and their role in chemosensitivity," Oncogene, 23, pp. 981-990, 2004.
Geissmann, F. et al., "Transforming growth factor beta1, in the presence of granulocyte/macrophage colony-stimulating factor and interleukin 4, induces differentiation of human peripheral blood monocytes into dendtritic Langerhans cells," Journal of Experimental Medicine, 187:6, pp. 961-966, 1998.
Jaksits S. et al., "CD34+ cell-derived CD14+ precursor cells develop into Langerhans cells in a TGF-beta beta 1-dependent manner," Journal of Immunology 163:9, pp. 4869-4877, 1999.
Caux, C. et al., "Respective involvement of TGF-beta and IL-4 in the development of Langerhans cells and non-Langerhans dendritic cells from CD34+ progenitors," Journal of Leukocyte Biology, Federation of American Societies for Experimental, 66:5, pp. 781-791, 1999.
Fairchild P.J. et al., "Directed differentiation of dendritic cells from mouse embryonic stem cells," Current Biology, Current Science, 10:23, pp. 1515-1518, 2000.
Paglia P. et al., "Immortalized Dendritic Cell Line Fully Competent in Antigen Presentation Initiates Primary T Cell Responses in Vivo," Journal of Experimental Medicine, 178:6, pp. 1893-1901, 1993.
Banchereau J. et al., "Immunobiology of Dendritic Cells," Annual Review of Immunology, Annual Reviews Inc., 18, pp. 767-811, 2000.
Ozawa H. et al., "Granulocyte-macrophage colony-stimulating factor gene transfer to dendritic cells or epidermal cells augments their antigen-presenting function including induction of anti-tumor immunity," Journal of Investigative Dermatology, 113:6, pp. 995-1005, 1999.
Masterson A. et al., "MUTZ-3, a human cell line model for the cytokine-induced differentiation of dendritic cells from CD34+ precursors," Blood, 100(2):701-703, Jul. 15, 2002.
Akashi et al., "Effects of interleukin-4 and interleukin-6 on the proliferation of CD34+ and CD34- blasts from acute myelogenous leukemia," Blood, vol. 78, pp. 197-204, 1991.
Bruserud et al., "Effects of γ-Irradiation on Acute Myelogenous Leukemia Blasts: In Vitro Studies of Proliferation, Constitutive Cytokine Secretion, and Accessory Cell Function During T Cell Activation," Journal of Hematotherapy & Stem Cell Research, vol. 8, pp. 431-441, 1999.
Bernhard et al., "Generation of Immunostimulatory Dendritic Cells from Human CD34+ Hematopoietic Progenitor Cells of the Bone Marrow and Peripheral Blood," Cancer Research, vol. 55, pp. 1099-1104, 1995.
Cignetti et al., "CD34+ Acute Myeloid and Lymphoid Leukemia Blasts Can Be Induced to Differentiate Into Dendritic Cells," Blood, vol. 94, pp. 2048-2055, 1999.
Drexler et al., "Cytokine response profiles of human myeloid factor-dependent cell lines," Leukemia, vol. 11, pp. 701-708, 1997.
Eibl et al., "Dendritic Cells Generated From Blood Precursors of Chronic Myelogenous Leukemia Patients Carry the Philadelphia Translocation and Canlnducea CML-Specific Primary Cytotoxic T-Cell Response," Genes, Chromosomes and Cancer, vol. 20, pp. 215-223, 1997.
"Phorbol 12-myristate 13-acetate," Excerpt from Sigma Aldrich catalogue, online: www.sigmaaldrich.com printed Mar. 19, 2012.

Min et al., "Differential Responses of CD34-positive Acute Myelogenous Leukemic Blasts to the Costimulating Effects of Stem Cell Factor with GM-CSF and/or IL-3," Yonsei Med. J., vol. 36, pp. 26-36, 1995.
MacLeod et al., "Cohabiting t(12;22) and inv(3) Primary Rearrangements in an Acute Myelomonocytic Leukemia (FAB M4) Cell Line," Genes, Chromosomes and Cancer, vol. 16, pp. 144-148, 1996.
Nicolo et al., "UVB-induced apoptosis of human dendritic cells: contribution by caspase-dependent and caspase-independent pathways," Blood, vol. 97, pp. 1803-1808, 1997.
Oehler et al., "Culture requirements for induction of dendtritic cell differentiation in acute myeloid leukemia," Ann. Hematol., vol. 79, pp. 35-362; 2000.
Spanbroek et al., "IL-4 determines eicosanoid formation in dendritic cells by down-regulation of 5-lipoxygenase and up-regulation of 15-lipoxygenase 1 expression," PNAS, vol. 98, pp. 5152-5157, 2001.
Steube et al., "Constitutive protein expression of monocyte chemotactic protein-1 (MCP-1) by meylomonocytic cell lines and regulation of the secretion by anti-and proinflammatory stimuli," Leukemia Research, vol. 23, pp. 843-849, 1999.
Steube et al., "Multiple Regulation of Constitutive and Induced Interleukin 8 Secretion in Human Myelomonocytic Cell Lines," Cytokine, vol. 12, pp. 1236-1239, 2000.
Steinman, R., "The Dendritic Cell System and Its Role in Immunogenicity," Rev. Immunol. Methods, vol. 9, pp. 271-296, 1991.
Thurner et al., "Generation of large numbers of fully mature and stable dendritic cells from leukapheresis products for clinical application," J. Immunol. Methods, vol. 223, pp. 1-15, 1999.
Quentmeier et al., "Cloning of human thymic stromal lymphopoietin (TSLP) and signaling mechanisms leading to proliferation," Leukemia, vol. 15, pp. 1286, 2001.
Koeffler et al., "Phorbol Ester Effect on Differentiation of Human Myeloid Leukemia Cell Lines Blocked at Different Stages of Mutation," Cancer Research, 41, 919-926, 1981.
Koski et al, "Calcium ionophore-treated myeloid cells acquire many dendritic cell characteristics independent of prior V differentiation state, transformation status, or sensitivity to biologic agents," Blood, vol. 94, No. 4, pp. 1359-1371, Aug. 1999.
Entry for "cell line." in Alberts et al. Molecular Biology of the Cell (3rd ed.). New York: Garland Publishing, Inc. 1994, p. G-5.
Hulette et al, "Cytokine induction of a human acute myelogenous leukemia cell line (KG-1) to CD1 a+ dendritic cell phenotype," Archives of Dermatological Research, vol. 293, No. 3, pp. 147-158, Mar. 2001.
Choudhury et al, "Dendritic Cells Derived In Vitro From Acute Myelogenous Leukemia Cells Stimulate Autologous, Antileukemic T-Cell Responses. Blood," vol. 93, pp. 780-786, Feb. 1999.
Hsu et al, "Fundamental Ca2+ signaling mechanisms in mouse dendritic cells: CRAC is the major Ca2+ entry pathway," The Journal of Immunology, vol. 166, pp. 6126-6133, May 2001.
Reinhard et al., "Generation of dendritic cell-based vaccines for cancer therapy," British Journal of Cancer, vol. 86, pp. 1529-1533, May 2002.
Ludewig et al, "Role of dendritic cells in the induction and maintenance of autoimmune diseases," Immunological Reviews, vol. 169, pp. 45-54, 1999.
Sigma entry for P1585, http://www.sigmaaldrich.com/catalog/search/ProductDetail/SIGMAIP1585, printed on Jun. 26, 2008.
Harrison et al, "Stimulation of autologous proliferative and cytotoxic T-cell responses by leukemic dendritic cells derived from blast cells in acute myeloid leukemia," Blood, vol. 97, No. 9, pp. 2764-2771, May 2001.
Quentmeier et al, "MUTZ-3, a monocytic model cell line for interleukin-4 and lipopolysaccharide studies," Immunology, vol. 89, pp. 606-612, 1996.
Charbonnier et al, "Human acute myeloblastic leukemia cells differentiate in vitro into mature dendritic cells and induce the differentiation of cytotoxic T cells against autologous leukemias," Eur. J. Immunol. vol. 29, pp. 2567-2578, 1999.
Hajas et al, "Ne fenotypic, functional and electrophysiological characteristics of KG-1 cells," Immunology Letters, vol. 92, pp. 97-106, 2004.

(56) References Cited

OTHER PUBLICATIONS

Kikuchi, T., "Genetically modified dendritic cells for therapeutic immunity," Tohoku J Exp Med. vol. 208, No. 1, pp. 1-8, Jan. 2006.
Verma et al, "Gene therapy—promises, problems and prospects," Nature. vol. 389, No. 6648, pp. 239-242, Sep. 1997.
Edelstein et al, "Gene therapy clinical trials worldwide 1989-2004—an overview," J Gene Med. vol. 6, No. 6, pp. 597-602, Jun. 2004.
Luo et al, "Synthetic DNA delivery systems," Nat Biotechnol. vol. 18, No. 1, pp. 33-7, Jan. 2000.
Karfan-Dabaja, M. et al, "Differentiation of acute and chronic myeloid leukemic blasts into the dendritic celilineage," Cancer Immunol Immunother, vol. 54, pp. 25-36, 2005.
Kim et al, "Impaired responses of leukemic dendritic cells derived from a human myeloid cell line to LPS stimulation," Exp Mol Med. vol. 38, No. 1, pp. 72-84, Feb. 2006.
Chen et al, "Interferon alpha in combination with GM-CSF induces the differentiation of leukaemic antigen-presenting cells that X have the capacity to stimulate a specific anti-leukaemic cytotoxic T-cell response from patients with chronic myeloid leukaemia," Br J Haematol. vol. 111, No. 2, pp. 596-607, Nov. 2000.
Smit et al, "Generation of dendritic cells expressing bcr-abl from CD34-positive chronic myeloid leukemia precursor cells," Hum Immunol. vol. 53, No. 2, pp. 216-223, Apr. 1997.
Canque et al, "IL-4 and CD40 ligation affect differently the differentiation, maturation, and function of human CD34+ cell-derived CD1a+CD14- and CD1a-CD14+ dendritic cell precursors in vitro," J. Leukoc Biol. vol. 64, No. 2, pp. 235-244, Aug. 1998.
Masterson et al., "Cytokine-induced differentiation of functional dendritic cells from the human acute myeloid leukemia cell line MUTZ-3," Proceedings of the American Association for Cancer Research Annual Meeting, Abstract #2772, vol. 43, p. 558, Mar. 2002.
Rosenzwajg, M. et al., "Human dendritic cell differentiation pathway from CD34+ hematopoietic precursor cells," *Blood*, 87:535-544 (1996).
Mackensen, A. et al., "Delineation of the dendritic cell lineage by generating large numbers of Birbeck granule-positive Langerhans cells from human peripheral blood progenitor cells in vitro," *Blood*, 86:2699-2707 (1995).
Fong, L. et al., "Dendritic Cells in Cancer Immunotherapie," Annu. Rev. Immunol., 18:245-273 (2000).
Kruisbeek, A., Research Report, DCPrime BV, The Netherlands. (Date unknown), printed as pp. 1/8-8/8.
Beyer, M. et al., "High-Resolution Transcriptome of Human Macrophages," *PLoS ONE* 7:9 e45466. Doi:10.1371/journal.pone.0045466, published Sep. 21, 2012, available online at www.plosone.org.
Pinzon-Charry, A. et al., "Dendritic cell dysfunction in cancer: A mechanism for immunosupression," *Immunology and Cell Biology*, 83:451-461 (2005).
Rickmann M. et al., "Monitoring dendritic cell and cytokine biomarkers during remission prior to relapse in patients with FLT3-ITD acute myeloid leukemia," *Ann Hematol*, 92:1079-1090 (2013).
Rickmann M. et al., "Elevated frequencies of leukemic myeloid and plasmacytoid dendritic cells in acute myeloid leukemia with the FLT3 internal tandem duplication," *Ann Hematol*, 90:1047-1058 (2011).

* cited by examiner

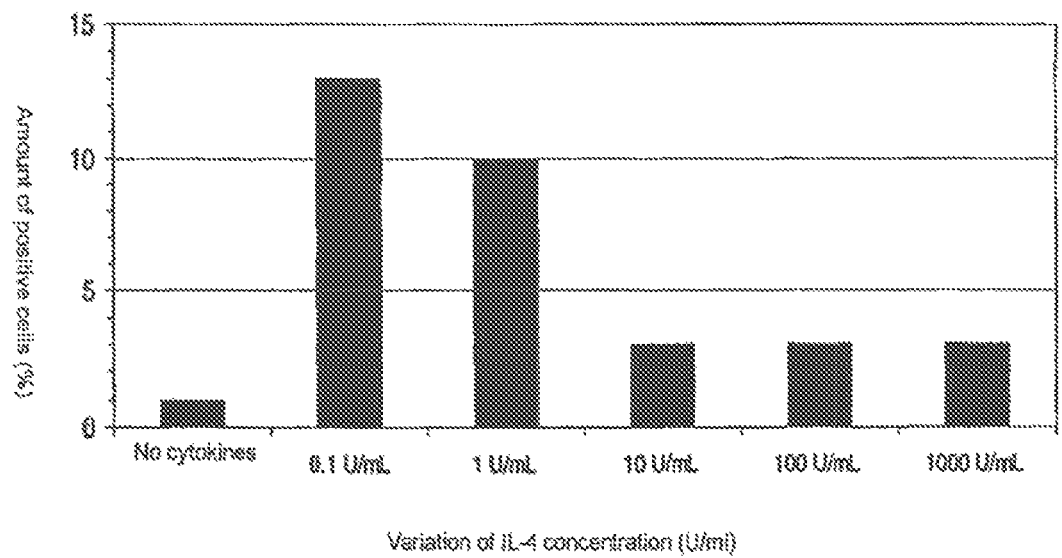

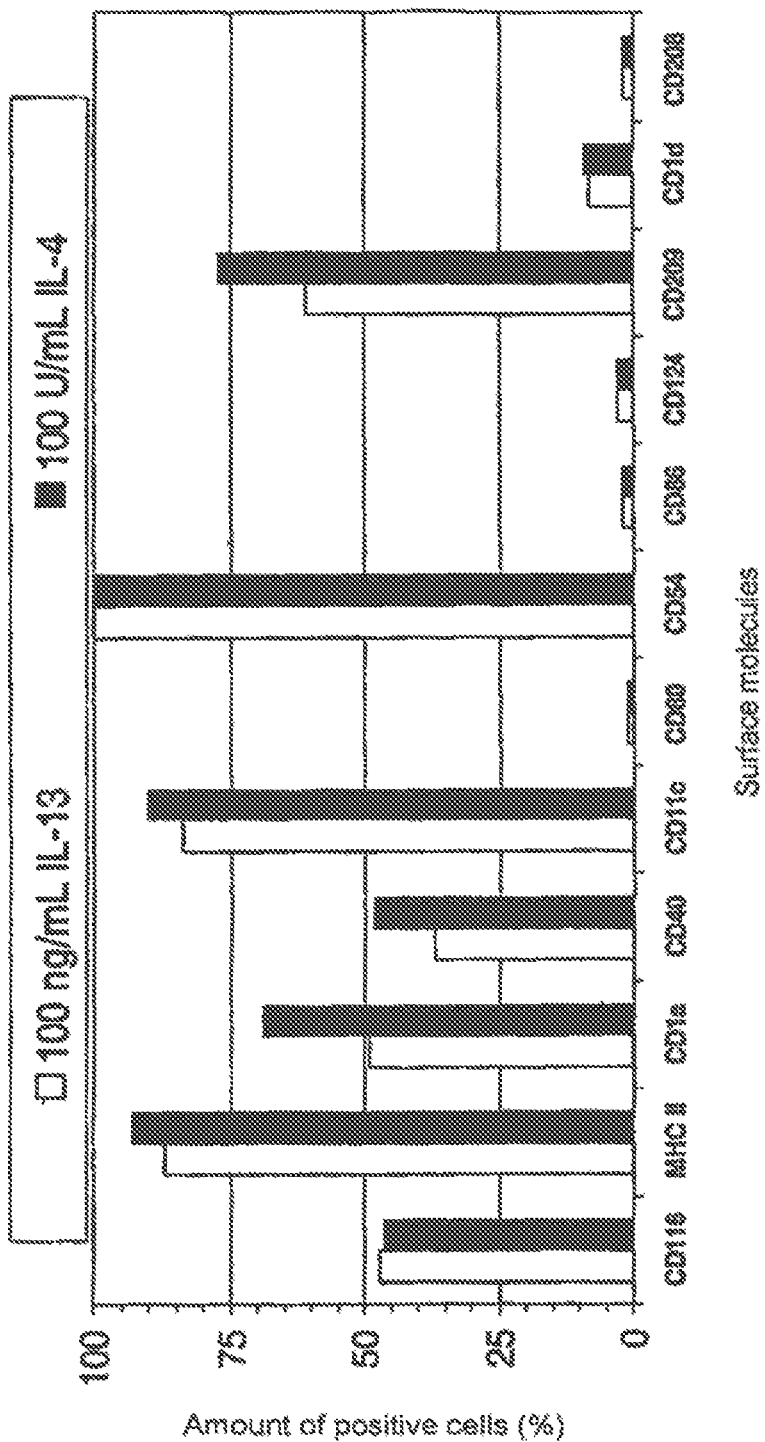

MUTZ-3 DENDRITIC CELLS

This application is a divisional application of U.S. application Ser. No. 10/486,966, filed Aug. 23, 2004, now U.S. Pat. No. 8,455,253, which is a national stage application of PCT/EP02/09260 filed Aug. 19, 2002, which claims priority under 35 U.S.C. §119 of German application No. 101 39 428.4, filed Aug. 17, 2001, the entirety of which are all incorporated by reference herein.

The instant application contains a Sequence Listing which has been submitted in ASCII format via EFS-Web and is hereby incorporated by reference in its entirety. Said ASCII copy, created on Apr. 12, 2013, is named "Sequence Listing Submitted in the parent case.txt" and is 4.00 kilobytes in size.

The invention describes the production and use of CD124+ and CD116+ cell lines for the production of effective dendritic cells (DC) using stimulatory molecules, their use in the production of allogenic or semi-allogenic immunotherapeutic agents and the use thereof in the treatment or prophylaxis of immune diseases. Furthermore, the invention describes the use of CD124+ and CD116+ tumor cell lines, preferably also being CD34+, as model and test systems for testing the DC biology and for testing substances having an impact on the immune system and on the conditioning thereof.

Dendritic cells (DC) play an important role as antigen-presenting cells (APC). They transmit co-stimulatory signals required for T cell activation and induce primary immune responses by presenting antigens to $CD4^+$ and $CD8^+$ T cells (Banchereau et al. 1998, Nature 392 (6673), 245-252). DCs develop from hematopoietic precursor cells in the bone marrow, going through sequentially different stages of differentiation (intermediary precursor cells in blood and immature DCs in peripheral tissues and organs) (Banchereau et al. 2000, Ann. Rev. Immunol. 18, 767-811). Once having reached the tissue, immature DCs (iDC) assume an important sensor function which is characterized by a high active uptake of antigens from the surrounding medium. Following stimulation by external signals ("danger signals") such as bacterial or viral infections or inflammatory processes, the DCs migrate into the peripheral lymphatic organs, there undergoing differentiation into mature DCs, and activating T cells by presenting antigens.

According to previous methods for the in vitro production of DCs, two major populations of DC precursor cells are obtained: $CD1a^+/CD14^-$ cells developing into Langerhans cells (LC), and $CD1a^-/CD14^+$ cells differentiating into interstitial DCs. Following culturing with GM-CSF and IL-4, monocytes can develop a phenotype which is similar to that of immature DCs (iDC). Further differentiation and maturing is achieved by various stimuli such as bacterial lipopolysaccharides (LPS), TNFalpha, PGE2, CD40 ligand or polyIC. Well-defined culturing systems available so far have been used to investigate the DC biology. However, their use in large-scale experiments is limited, depending on the availability of donor material and the variability thereof. In the murine system, cytokine (GM-CSF)-dependent dendritic cell lines were found to be highly valuable when studying the DC differentiation and development in in vitro and in vivo disease models. Such cell lines were obtained by immortalization of murine lymphatic or cutaneous tissues. They represent an immature DC phenotype, which is invariable, and therefore do not allow investigations concerning various factors involved in DC differentiation. Furthermore, due to the heterogeneity of DCs in the murine and human systems, statements as to the DC biology in humans, if at all, are only possible to a very limited extent.

It has been observed that tumors of lymphoid or myeloid origin have features in common with APC in the ontogenesis. Studies on PBMC from patients suffering from chronic myeloid leukemia (CML) and acute myeloid leukemia (AML) have shown that cytokines in subpopulations of CML and AML blast cells achieve a somewhat DC-similar differentiation exhibiting enhanced APC function in part. Consequently, attempts have been made to use established leukemic cell lines as in vitro model systems in investigations regarding the DC biology. However, no success has been achieved in this respect because all of the investigated cell lines were only capable of reaching specific stages of DC development beyond which further differentiation thereof was not possible, thus failing to reflect the DC biology as desired. This is due to the fact that the capability of such malignant cells of responding to cytokine stimuli depends on the expression of specific and functional receptors. However, many leukemia cell lines do not respond to cytokine treatment. Other leukemia cell lines examined so far only respond to treatment with particular cytokines and cannot be developed into effective DCs by sequential DC differentiation. While pharmacological agents mobilizing intracellular calcium and thus avoiding corrupted receptor signal pathways can be used to induce a DC-like phenotype in myeloid cells—the activation of protein kinase C by PMA induces a DC phenotype in the human myeloblast cell line KG-1—manipulation of intracellular signal pathways by means of such agents results in APCs failing to cover the full DC function. Thus, in the case of cytokine-stimulated KG-1, no differentiation without immediate maturing has been observed, for example.

As a consequence, all of the cell lines investigated up to now have only limited suitability for use in investigations directed to the DC biology. They are not suitable for immunotherapeutic uses and in test systems for testing substances having an impact on the immune system. The state of the art therefore implies that leukemic cell lines or other tumor cell lines would not be capable of differentiating into immature DCs by corresponding stimulation, said DCs—depending on the stimulation—being similar either to interstitial DCs or Langerhans DCs, and subsequently into potent mature DCs, specifically either DC type 1 or DC type 2.

At present, DCs are being used in various procedures and approaches to treat various diseases, including e.g. tumor diseases, infectious diseases, and autoimmune diseases. The results indicate success and are promising. In all such treatments, however, DCs recovered from primary cells have to be used at present because, despite great efforts, no success has been achieved in generating and identifying cell lines that would allow production of DCs stimulating an effective immune response. For example, the disadvantages of DCs from primarily cells are the following: DCs or their precursor cells can be obtained from patients or donors only in very low quantities, thus severely limiting the use of these cells; their recovery requires a high input of time and work; the amount of recovered DCs is exceedingly small, so that nowhere near proportional amounts could be employed in humans that achieve greatest success of treatment in murine models. The DCs have to be obtained from precursor cells, such as CD34-positive stem cells or monocytes, maturing in vitro by suitable stimulation with stimulatory molecules to form DCs, said precursor cells being extremely rare both in blood and tissue. Their contribution to the PBMC is estimated to be about 1%. Furthermore, culturing thereof is difficult, being severely restricted by the amount of monocytes recovered from the PBMC and frequently impaired by progenitor cell impurities. The resulting large variance in the efficiency of purification, stimulation and effectiveness of autologous DC precursor cells massively impedes the standardization of methods for use in immunotherapeutic treatment. In addition to the variance within a patient, there is a variance from one particular individual to another.

To develop immunotherapeutic agents based on effective DCs, it is advantageous to generate precisely characterized cell lines which either represent effective DCs or can be transformed in vitro into such by means of appropriate stimulation using suitable signal molecules, which DCs can then be used alone or in combination with other substances to provide effective immunotherapeutic agents.

The object of the invention is therefore to provide a method of producing cell lines or cells allowing generation of effective dendritic cells (DC) therefrom which can be used particularly as immunotherapeutic agents or as part of immunotherapeutic agents in the treatment of immune diseases.

The invention solves this technical problem by providing a method of producing effective dendritic cells or cell lines, wherein cells from CD124- and CD116-positive cell lines are contacted simultaneously or in a sequentially deferred fashion with at least one stimulatory molecule, thus obtaining the effective dendritic cells or cell lines.

In connection with this invention the following terms will be used as follows:

Cell lines from which effective dendritic cells (effective DC) are obtained according to the invention include all tumor cell lines, preferably leukemia cell lines, such as myeloid, lymphoid and plasmacytoid lines, as well as cell lines of non-leukemic origin, but bearing CD124 and CD116, and preferably CD34 as well, including such cell lines which are not tumor cell lines in the strict sense. Also possible are cell lines lacking CD124 and/or CD116, but expressing functional recombinant CD124 and CD116 as a result of incorporating genes, thus enabling production of effective DCs. Preferably, the cell lines from which effective DCs are obtained are also CD34-positive, and said CD34 can also be incorporated by means of genes. Such cell lines, from which effective DCs are produced, can be obtained from tumor cells or primary cells. This is effected by means of per se conventional methods such as transformation, immortalization, cell fusion with tumor cells and/or culturing in vitro or in vivo with or without cloning of cells of preferably homogeneous cell lines. Those methods are preferred wherein CD124- and CD116-positive cells are accumulated and cloned by means of magnetic ball techniques or cell sorting in an FACS according to per se known procedures. Patients suffering from chronic myeloid leukemia or acute myeloid leukemia are preferred as donors of tumor cells which, according to the invention, are transferred into cell lines by stimulatory molecules, from which effective DCs are obtained; however, the invention is not restricted thereto. Primary cells from which suitable cell lines are obtained are preferably of myeloid, lymphoid, plasmacytic or monocytic origin. To obtain effective DCs from cell lines and/or increase the effectiveness of the DCs obtained, one or more genes can be incorporated in the cell lines, tumor cells or primary cells according to per se known methods, which genes encode and/or express e.g. receptors for or inhibitors of stimulatory molecules. It is also possible to introduce one or more immunotherapeutic agents in the form of genes. Introduction of the immunotherapeutic agent genes at this stage of the cell line is advantageous in that the genes can be characterized as a cell line and do not have to be introduced subsequent to maturing into dendritic cells for further use as immunotherapeutic agents. Another way of introducing genes is fusion of the cell lines with other cells or cell lines according to per se known methods.

According to the invention, effective DCs are understood to be such cells or cell lines which, as a result of stimulation of cell lines with stimulatory molecules, differentiate into cells acting like dendritic cells, activating, inhibiting or modulating humoral and/or cellular portions of the immune system. Such effective DCs are used as immunotherapeutic agents. To this end, the effective DCs, the precursor cells thereof at a suitable stage of differentiation, or the cells of the cell lines are loaded with at least one antigen. Such loading is effected according to per se known methods, e.g. by loading with tumor antigens or infection antigens, synthetic or purified or partially purified from biological material, with cell lysates of tumor cells, tumor cell lines, infected cells or cell lines, by fusion with other cells or cell lines, by introducing at least immunotherapeutic gene, by infection with infectious particles or portions thereof. Optionally, the loaded cells or cell lines are subjected to further differentiation by stimulatory molecules. In general, the effective DCs will process the antigens, presenting them to the corresponding immune cells of the immune system via particular molecules, e.g. via MHCI or MHCII molecules, thereby correspondingly activating the humoral and/or cellular immune response which combats the disease or builds up an immunological memory preventing diseases in a prophylactic fashion. For this purpose, the effective DCs are used at at least one suitable activity and/or effector stage in the patient as immunotherapeutic agent.

According to the invention, stimulatory molecules are understood to be those chemical and biological molecules which influence the differentiation of cells, such as cytokines (IL-4, TNFalpha), growth factors (e.g. GM-CSF), surrogate molecules for cytokines or growth factors inducing a biological effect comparable to that of the stimulatory molecules themselves, e.g. antibodies, other biological molecules (e.g. LPS, polyIC), and chemical agents. The molecules can be employed together at the same time or in a sequentially deferred fashion so as to achieve the corresponding desired differentiation stage of the cells and thus different activity and effector stages, e.g. DC type 1 or DC type 2 phenotype cells which can be employed for each of the various uses, depending on the suitability thereof. Using different stimulatory molecules, for example, it is possible to produce DCs of varying effectiveness from the same initial tumor cell line, which DCs e.g. have an inhibitory or stimulatory effect on different components of the immune system and are thus used e.g. in the immunotherapy of infectious diseases, tumor diseases or autoimmune diseases. According to the invention, stimulatory molecules are also understood to include all danger signals, even those which are not molecules in a strict sense, such as mechanical stress, for example.

According to the invention, immunotherapeutic agents are understood to be those therapeutic agents which can be used against diseases in a prophylactic or curative fashion where the use of effective dendritic cells for treatment is possible, and suitable effective dendritic cells can involve varying stages of development and activation. The success of treatment can be complete or partial, and the agents can also be vaccines, for example.

According to the invention, semi-allogenic DCs are those effective DCs matching in one or more of the HLA molecules with the recipient of the immunotherapeutic agents, with the cells not being derived from the same person. Thus, this also includes those DCs which exhibit complete matching in the HLA molecules and are not derived from the same person.

According to the invention, allogenic DCs are those effective DCs matching in none of the HLA molecules with the recipient of the immunotherapeutic agents.

According to the invention, CD124-positive cell lines or cells are understood to be those cells which are sensitive to treatment with IL-4.

According to the invention, CD116-positive cell lines or cells are understood to be those cells which are sensitive to treatment with GM-CSF.

According to the invention, immune diseases are understood to include all those diseases allowing the use of dendritic cells for treatment, for instance:
- infectious diseases,
- tumor diseases,
- autoimmune diseases.

According to the invention, introduction of genes is understood to be transfection or viral infection or transformation of cells or cell lines, thereby introducing genetic material into the cell or cell lines according to per se known methods. The genetic material can be DNA or RNA. The genetic material codes for the expression of at least one protein or peptide, or/and the RNA itself can have an inhibitory or stimulatory effect, e.g. as an antisense RNA. The proteins being expressed can be further processed and modified, e.g. by glycosylation. Genes can also be introduced by fusing cells or cell lines with other cells or cell lines.

According to the invention, immunotherapeutic agent genes are genes encoding proteins and/or peptides which play a role in the use of the effective dendritic cells as immunotherapeutic agents, e.g. tumor antigens, viral antigens or antigens from parasites, bacteria or other microorganisms. Cells or cell lines having immunotherapeutic agent genes incorporated therein will express the proteins or peptides of these genes, and these are presented to the immune system by the dendritic cells, so that the effective dendritic cells activate, inhibit or modulate corresponding immune responses, depending on the activity and effector stages of the effective dendritic cells. For presentation of the gene products, the expressed proteins or peptides are processed or directly used; furthermore, the expressed proteins or peptides can be modified, e.g. by glycosylation.

According to the invention, surrogate molecules are those molecules which are capable of replacing the stimulatory molecules as to the effect thereof; instead of cytokines, for example, it is possible to use antibodies or mimicry peptides which influence the cells in the same way as stimulatory molecules.

Cell apoptosis or necrosis to be caused according to the invention involves various methods as required, e.g. irradiation, thermal shock, mechanical stress, oxidative stress, ultrasound, induction of suicide genes, induction by chemical and biological molecules, glycerol, zinc, butilinic acid, sodium butyrate, leptomycin B with STI571 and/or Fas ligand. The cells may also form mixed populations, part of which undergoing apoptosis or necrosis. This method can be used to make sure that effective dendritic cells are not viable in the organism.

According to the invention, tumor antigens are peptides, proteins, lipids, lipopeptides, lipoproteins, carbohydrates, glycolipids, glycopeptides, glycoproteins, phosphorylated proteins, phosphorylated peptides, proteins or peptides otherwise modified following translation, which, compared to normal tissue, are overexpressed in the cells of the tumor, underexpressed, expressed de novo, mutated, differentially modified after translation, differentially processed, differentially situated, differentially folded, or otherwise modified.

According to the invention, infection antigens are peptides, proteins, lipids, lipopeptides, lipoproteins, carbohydrates, glycolipids, glycopeptides, glycoproteins, phosphorylated proteins, phosphorylated peptides, proteins or peptides otherwise modified following translation, which are derived from an infectious particle.

According to the invention, infectious particles are infectious moieties causing diseases, or portions derived therefrom, including e.g. viruses, bacteria, parasites, and prions. The infectious particles which, according to the invention, serve in the production and use of effective dendritic cells are not capable of propagating in vivo, i.e., in the patient.

Furthermore, the invention describes the production and use of CD124+ and CD116+ tumor cell lines, preferably also being CD34+, as model and test systems for testing the DC biology and for testing substances having an impact on the immune system and on the conditioning thereof.

According to the invention, model and test systems for testing the DC biology are understood to be test systems having as component a CD124+ and CD116+ tumor cell line, which is preferably also CD34+, and allowing the elucidation of processes during the differentiation of dendritic cells and of cells maturing into dendritic cells, and/or allowing the elucidation of processes influenced by the DCs or the precursor cells thereof during activation, inhibition or modulation of the immune system and its immune response. The elucidation of these processes also includes the elucidation of other influences, such as the influence of stimulatory molecules and/or their effect in time, e.g. during differentiation of the DCs and activity modulation of the immune system. Such model and test systems can be used in the form of kits and/or high-throughput systems, for example. The specific types of tests and the implementation thereof are well-known to those skilled in the art.

According to the invention, model and test systems for testing substances having an effect on the immune system are understood to be test systems having as component a CD124+ and CD116+ tumor cell line, which is preferably also CD34+, and allowing tests as to whether substances have an impact on the immune system and/or on the conditioning thereof. Inter alia, this also includes test systems serving in the development of immunotherapeutic agents, e.g. testing of suitable tumor vaccines and formulations thereof, as well as test systems allowing tests as to the influence of substances on the immune system, which are not immunotherapeutic agents, such as chemical substances, pharmacological agents, cosmetics or precursors thereof, or foodstuffs or components thereof. Consequently, such test systems can be used in the product development of e.g. immunotherapeutic agents and other products which may have an influence on the immune system. For example, these model and test systems can be used in the form of kits and/or high-throughput systems. The specific types of tests and the implementation thereof are well-known to those skilled in the art.

Cells positive to CD124 bear the receptor for IL-4, the CD116+ bear the receptor for GM-CSF, and the CD34+ bear the marker for hematopoietic stem cells and progenitor cells.

Another preferred embodiment of the invention is a method for the identification of peptides presented by the effective dendritic cells according to the invention, comprising the steps of (a) propagating the inventive dendritic cells according to per se known methods, said dendritic cells being immature cells;

(b) adding antigens or immunogens or portions thereof or cell lysates, whereby the immature dendritic cells (iDC) develop into mature dendritic cells (mDC), processing the antigens or immunogens or portions thereof or the cell lysates and presenting suitable peptides in the context of class I MHC or class II MHC molecules;

(c) recovering the presented peptides from the dendritic cells according to per se known methods; and
(d) identifying/determining the removed peptides according to per se known methods.

The peptides obtained are preferably separated using per se known methods, e.g. by means of high-pressure liquid chromatography (HPLC). In a particularly preferred fashion, the separated peptides are identified by mass spectrometry, and most preferably the peptides are subjected to sequencing.

The method according to the invention preferably allows for validation of the identified/determined peptides. More preferably, the identified/determined peptides obtained according to the method of the invention are produced by synthesis according to per se known methods. Most preferably, the peptides produced by synthesis are added to immature and/or mature dendritic cells according to the invention, the dendritic cells being loaded ("pulsed") according to per se known methods. In one variant, the following step is carried out instead of step (b): Loading of cells matured into mDCs with MHC I and/or MHC II peptides. This step can be preceded by a step of removing existing MHC I and/or MHC II peptides according to per se known methods. In a preferred fashion, libraries of MHC I and/or MHC II peptides are presented to the mDCs.

Surprisingly, leukemic cell lines having a specific property have been found with the aid of this invention, which function in all aspects like an immortalized equivalent of CD34+ DC precursor cells and are suitable for use in investigations of the DC biology, testing of substances influencing the immune system, and in immunotherapeutic agents. The specific properties of the tumor cell lines involve positiveness to CD124 (IL-4R) and CD116 (GM-CSFRalpha) and preferably CD34. As an example, the myeloid cell line MUTZ-3 will be described in more detail, which recently has been reported to down-regulate the expression of CD14 upon stimulation with IL-4 and GM-CSF. The investigations of this invention demonstrate that, compared to other well-known and tested leukemic cell lines and other tumor cell lines, MUTZ-3 cells are unique in their capability of attaining an immature DC state. Moreover, they express the maturing marker CD83 upon further stimulation, and functional assays prove their capability of antigen processing and presentation. Therefore, they are suitable for immunotherapeutic purposes. MUTZ-3 is the first human leukemia cell line which can be stimulated so as to undergo differentiation and formation of an immature DC phenotype, and which is suitable as an in vitro model for use in investigations relating to the molecular and physiological pathways leading to differentiation and maturing of DCs and in investigations on the DC biology and in testing of substances influencing the immune system.

Within the context of this invention it will be demonstrated in a surprising fashion that effective DCs can be generated from human tumor cell lines which, in particular, can be used as immunotherapeutic agents or as a component of immunotherapeutic agents in the treatment of immune diseases. Key features of the cell lines are their positiveness to CD124 and CD116 which can be obtained from leukemic cells, for example, and the sensitivity to stimulatory molecules such as cytokines, whereas other investigated leukemia cell lines lacking these properties fail to provide effective DCs in the meaning of the invention. Preferred is a cell line by means of which it is possible to obtain DCs of different activation and effector stages from said cell line by sequential stimulation with stimulatory molecules. The individual activation and effector stages can be used as effective DCs to activate various portions of the immune system, activating CD8+ T cells via MHCI presentation, activating CD4+ T cells via MHCII presentation, or activating NKT cells via CD1. Activated DCs are mainly employed in immunotherapeutic agents used in the treatment of infectious diseases and tumor diseases. Furthermore, suitable DC activation stages may give rise to induction of anergies and tolerances and are also suitable in the treatment of autoimmune diseases.

With reference to the example of the human myeloid cell line MUTZ-3, the invention will be described in more detail below.

The human acute myeloid leukemia cell line MUTZ-3 is sensitive to those cytokines which are responsible for the generation of DCs from monocytes and CD34 positive stem cells in in vivo and in vitro models. In all their properties, MUTZ-3 cells behave as immortalized equivalents of CD34-positive DC precursor cells. When stimulated using the respective suitable specific cytokine cocktail, they develop into cells having phenotypes corresponding to the phenotypes of e.g. interstitial DCs or Langerhans cells. As a result of maturation these cells express CD83. MUTZ-3 have the complete spectrum of antigen processing and presentation processes for MHC-dependent and CD1d-dependent presentation and activation. Under suitable conditions, e.g. administration of interferon-gamma or dexamethasone, they are capable of specifically adopting a DC1 phenotype or a DC2 phenotype, thereby allowing controlled immune response. Thus, it is evident that MUTZ-3 cells represent an unlimited source of CD34-positive DC precursor cells (progenitors) which can be used efficiently in (directed) stimulation of various immune cells and thus as effective DCs in the treatment of immune diseases.

The component of immunotherapeutic agents, which is important in the meaning of the invention, is the cell line representing effective DCs itself or forming effective DCs upon treatment with suitable stimulatory molecules. In the meaning of the invention, the effective DCs can be combined with other components to form allogenic or semi-allogenic immunotherapeutic agents, and, if required, further maturing of the cells is possible, optionally using suitable stimulatory molecules. In Example 1 this will be described for the case of MUTZ-3, with MHCI-, MHCII- and CD1-mediated activation each time. However, the invention is not restricted thereto, but also comprises all therapeutic or prophylactic fields of use where DCs can be employed.

This also includes tumor therapeutic agents, for example. These agents can be produced in such a way that e.g. the allogenic or semi-allogenic effective DCs are pulsed e.g. with tumor antigens according to per se known methods and administered to patients. Such tumor antigens can be one or more well-defined molecules such as peptides, glycopeptides, proteins, glycoproteins, glycolipids which are synthesized, purified, or used in the form of cell lysates; another example is transfection of effective DCs with RNA, DNA or viral vectors encoding tumor antigens or portions thereof; another example is antigen loading of effective DCs by incubation with apoptotic and/or necrotic tumor cells or with thermal shock-treated cells; a further example is fusion with tumor cells. Clinical use of such DCs produced within the scope of the invention is effected in the form of allogenic or semi-allogenic DCs, prophylactic or as a curative therapy, e.g. in tumor therapy or following removal of such tumors e.g. by surgery, as an adjuvant therapy for the treatment of minimal residual diseases, including combating metastases or preventing formation of metastases or micro-metastases.

A number of immunization strategies are possible, such as intranodal, intratumoral, intradermal, intramuscular, subcutaneous, intraperitoneal, or mucosal application of DCs, in the presence or absence of additional immunostimulants such as cytokines, chemokines or other immunostimulatory or immunomodulatory substances. The DCs produced according to the invention may also be part of a more complex immunization regimen wherein e.g. further components are administered simultaneously or in a deferred fashion.

Although DCs derived from MUTZ-3 no longer undergo division following differentiation, it is not impossible that DCs produced from other leukemia cells or lines will divide further. One preferred variant is therefore irradiation of such antigen-loaded DCs, treatment thereof with mitomycin C, or other measures preventing cell division in vivo. For example, one alternative would be incorporation of a so-called suicide gene, such as HSV thymidine kinase (TK) gene, allowing selective destruction of the HSV TK-bearing cells by means of gancyclovir.

The invention also relates to the production of cell lines which can be matured into effective DCs. The method of the invention involves isolation of CD34+, CD124+ and CD116+ cells from human material, preferably from leukemia patients, according to per se known methods. For example, the cells can be recovered sequentially from peripheral blood or bone marrow of leukemia patients by accumulation of cells, which are CD34+, CD124+ and CD116+, using magnetic beads bearing antibodies for CD34+, CD124+ and CD116+. Alternatively, CD34+, CD124+ and CD116+ cells can be obtained by cell sorting using flow cytometry and CD34-, CD124- and CD116-specific antibodies.

Another embodiment of the invention is a method of producing a drug, comprising the steps of the method according to the invention and further comprising the step of formulating the drug in a pharmaceutically tolerable form, the drug optionally being combined with an additional adjuvant as an active substance enhancer.

According to the invention, the term "drug" defines substances and formulations of substances intended to cure, alleviate or avoid diseases, illness, physical defects or pathological affection by application on or in the human body. During the production process of the invention, medical and/or pharmaceutical-technical adjuvants can be added to the compounds identified by means of the method according to the invention. According to the invention, medical adjuvants are substances used (as active components) in the production of drugs in a process according to the invention. Pharmaceutical-technical adjuvants merely serve to formulate the drug and, if required during the process only, can even be removed thereafter, or they can be part of the drug as pharmaceutically tolerable carriers. Examples of pharmaceutically tolerable carriers are given below.

Drug formulation is optionally effected in combination with a pharmaceutically tolerable carrier and/or diluent.

Examples of suitable pharmaceutically tolerable carriers are well-known to those skilled in the art and include phosphate-buffered saline solutions, water, emulsions such as oil/water emulsions, various types of detergents, sterile solutions, etc.

Drugs comprising such carriers can be formulated by means of well-known conventional methods. Those routes of application are preferred where the inventive effective dendritic cells in a pharmacological formulation are delivered to sites within the body where they assume their function in the best way possible. Such sites and routes of application are well-known to those skilled in the art, e.g. intravenous, intraperitoneal, subcutaneous, intramuscular, local or intradermal, with intranodal, intradermal, subcutaneous, intrarectal, intravenous or local being preferred. A suitable route of application may exhibit varying suitability, depending on the particular disease.

For example, application of effective dendritic cells for the therapy of autoimmune diseases is directed to tolerance of the immune system, whereas a suitable route of application for the treatment or prophylaxis of tumor or infectious diseases is intended to support activation of the immune system. Those skilled in the art will be able to determine suitable routes of administration by means of per se known methods. The drugs can be administered to an individual in a suitable dose, one dose comprising from 100 to $10^{12}$ effective dendritic cells, preferably from $10^5$ to $10^{10}$. The effective dendritic cells are loaded with a suitable form and quantity of antigens which also may vary depending on the type of use. A single dose is preferably administered once a week and up to greater intervals of e.g. one month, 3 months, one year or even longer intervals. Shorter intervals may also be suitable, e.g. once per day. Those skilled in the art will be able to determine suitable time intervals and doses, preferably using methods of immuno-monitoring and adjusting the doses correspondingly. Suitable methods are well-known to those skilled in the art, and some of them will be described in the examples.

The kind of dosage will be determined by the attending physician according to the clinical factors. As is familiar to those skilled in the art, the kind of dosage will depend on various factors, such as size, body surface, age, sex, or general health condition of the patient, but also on the particular agent being administered, the time period and type of administration, and on other medications possibly administered in parallel.

In a preferred embodiment the effective dendritic cells are loaded with a number of antigens. In another preferred embodiment doses of effective dendritic cells loaded with suitable antigens are combined with doses directly comprising the antigens or single antigens or portions thereof in suitable formulations, with no ex vivo loading of dendritic cells. This is advantageous in that semi-allogenic ex vivo loaded inventive dendritic cells strongly induce immune response, being supported by the alloresponse as a kind of danger signal and associated with partial specific immunization by presentation of overlapping MHC molecules, and combined with an immune response directed to the dendritic cells in vivo. Such a combination is particularly suitable in breaking up tolerances and anergies.

In a preferred embodiment inventive immature effective dendritic cells (iDC form) loaded with a corresponding antigen are used for the treatment of autoimmune diseases. In another preferred embodiment the cells are locked in the iDC form in a transient or stable fashion, for which purpose methods are used that are well-known to those skilled in the art, e.g. locking by genetically engineered modifications. In another preferred embodiment, following loading in the immature form (iDC) or mature form (mDC), the cells are further matured and used as loaded effective dendritic cells (mDC) in the treatment or prophylaxis of tumor or infectious diseases.

A drug according to the invention comprises a pharmacological substance which contains the dendritic cells in a suitable solution or administration form. Administration thereof can be effected either alone or in combination with one or more adjuvants or other suitable material enhancing the drug effect. QS-21, GPI-0100 or other saponins, water-oil emulsions such as Montanide adjuvants, polylysine, polyarginine compounds, DNA compounds such as CpG, Detox, bacterial vaccines such as typhoid vaccine or BCG vaccines are used as preferred adjuvants and mixed with the dendritic cells of the invention in a suitable manner according to per se known methods.

Preferred forms of adjuvants are co-stimulatory factors, cytokines and/or growth factors such as GM-CSF or IL-2 or IL-12. They can also be incorporated in a genetic form in the cells of the cell lines according to the invention, preferably in a stable fashion.

The inventive use of the drug is in the prophylaxis and/or treatment of cancerous diseases, tumors, infections and/or autoimmune diseases. In a preferred embodiment the cancerous disease or the tumor to be treated or prevented is selected from the group of cancerous diseases or tumor diseases of head and nape, lungs, mediastinum, gastrointestinal tract, sexual apparatus/urinary system, gynecological system, breast, endocrine system, skin, cancerous diseases or tumor diseases during childhood, primary tumors, metastasizing cancer, soft-tissue sarcoma or osteosarcoma, melanoma, neoplasms of the central nervous system, lymphoma, leukemias, paraneoplastic syndrome, peritoneal carcinomatosis and/or malignancy related to immunosuppressed malignancy.

The infection to be treated or prevented with the drug of the invention is selected from bacterial infections, viral infections, fungous infections, infections with protozoa and/or infections with helminths. In a preferred fashion, the bacterial, viral, fungous infection, infection with protozoa and/or infection with helminths, which is to be treated or prevented, is selected from infections such as sepsis or septic shock, fever of unknown origin, infectious endocarditis, intra-abdominal infections and abscesses, acute infections, diarrhea diseases, bacterial food poisoning, sexually transmittable infections, inflammatory pelvis infections, urinary tract infections, pyelonephritis, osteomyelitis, infections of the skin, muscles or soft tissue, infections by injection of drugs, infections by bites, scratches or burns, infections in graft recipients, hospitalism infections and/or intravascular infections caused by equipment. In a more preferred embodiment the infection to be prevented or treated is selected from bacterial infections such as pneumococcal infections, staphylococcal infections, streptococcal infections, enterococcal infections, diphtheria, various corynebacterial infections, anthrax, *Listeria monocytogenes* infections, tetanus, botulism, gas gangrene, antibiotics-associated colitis, various clostridial infections, meningococcal infections, gonococcal infections, *Moraxella* (branhamella) catarrhalis infections, infections with other *Moraxella* species, *Klingella* infections, *hemophilus influenza* infections, infections with other *hemophilus* species, infections with the HACEK group, infections by other gram-negative bacilli, *Legionella* infections, pertussis, infections by gram-negative enterobacteria, helicobacterial infections, infections by pseudomonades and related organisms, salmonellosis, shigellosis, infections by campylobacteria and related species, cholera, vibrio, brucellosis, tularemia, plague, various yersinia infections, Bartonella infections, including infections by cat scratches, Donovania (*Granuloma inguinale*), nocardiosis, actinomycosis, infections by multiple anaerobic organisms, tuberculosis, leprosy, infections by non-tubercle bacteria, syphilis, endemic treponematosis, leptospirosis, relapsing fever, Lyme borreliosis, infections by rickettsia, mycoplasmas or chlamydia, viral infections such as Herpes simplex virus infections, *Varicella zoster* infections, Epstein-Barr virus infections, including mononucleosis, cytomegalovirus infections, human Herpes virus type 6, 7 or 8 infections, smallpox virus infections, Vaccinia infections, various poxvirus infections, parvovirus infections, human papillomavirus infections, viral respiratory tract infections, influenza, viral gastroenteritis, enterovirus infections, reovirus infections, measles, rubella, mumps, rabies virus infections, other rhabdovirus infections, infections caused by rodent and/or arthropod viruses, infections with Marburg and/or Ebola viruses, fungous infections such as histoplasmosis, coccidioidomycosis, blastomycosis, cryptococcosis, candidiasis, aspergillosis, mucormycosis, miscellaneous mycoses, prototheca infections, *Pneumocystis carinii* infections, infections with protozoa such as ameba infestation, infections with free-living ameba, malaria, infections by parasites of red blood cells, Leishmaniosis, trypanosomiasis, toxoplasma infections, intestinal infections by protozoa, trichomonad colpitis, infections with helminths such as trichinosis, infections with other tissue nematoda, infections with intestinal nematoda, filariosis, infections such as loiasis, onchocercosis or dracontiasis, schistosoma, trematoda infections or cestoda infections.

The autoimmune disease to be treated or prevented by means of the drug according to the invention is selected from autoimmune diseases such as allergic encephalomyelitis, autoimmune hemolytic anemia, autoimmune thyroiditis (Hashimoto syndrome), autoimmune male sterility, pemphigoid, abdominal cave disease, Basedow disease, Goodpasture syndrome, idiopathic thrombocytopenic purpura, insulin-resistant diabetes mellitus, myasthenia gravis, pernicious anemia, pemphigus vulgaris, polyarteritis nodosa, primary bile cirrhosis, Reiter syndrome, rheumatic fever, sarcoidosis, Sjögren syndrome, systemic lupus erythematodes, sympathetic ophthalmia, multiple Sclerosis, and/or viral myocarditis by Cocksakie B virus response.

Another preferred embodiment of the invention is a method for the production of a drug, comprising the procedures according to the invention, said drug including dendritic cells loaded with antigens according to per se known methods or fused with corresponding cells. The dendritic cells of the drug are formulated with a suitable pharmaceutical carrier according to methods per se known in autologous dendritic cell therapy. The drug thus obtained can be administered according to per se known methods. The dendritic cells of the drug take up antigens, process them, and present fragments thereof on their surface in the context with MHC molecules and co-stimulatory molecules. Following further maturing according to per se known methods, the cells in suitable formulation are used in humans. Another example is loading of mature dendritic cells according to per se known pulsing methods. The dendritic cells are autologous, allogenic or semi-allogenic dendritic cells or precursor cells thereof, or cells from cell lines having the functional properties of dendritic cells, which cells are suitably treated ex vivo for development and maturing according to per se known methods.

If necessary, the precursor cells are preferably matured by adding suitable factors, e.g. co-stimulatory factors, cytokines and/or growth factors such as IL-4 and GM-CSF, to form cells which are similar to iDCs in terms of function and phenotype. These cells are loaded with suitable antigens and matured further, if required. The resulting loaded effective dendritic cells (mDC) are cells which are similar to loaded dendritic cells in terms of function and phenotype and are preferably used in the prophylaxis or therapy of tumor or infectious diseases. Alternatively, it is also possible to load the effective dendritic cells at a later stage as mDCs, e.g. in case of well-defined MHC class peptides as antigens. Alternatively, cells at varying precursor, differentiation and/or maturing stages can be transfected with DNA or RNA of antigens, co-stimulatory molecules and/or immunogens according to per se known methods of genetic engineering. Preferably, these are stable trans-formations of those cells undergoing division in the best way possible, preferably prior to the precursor stage and prior to differentiation. Alternatively, suitable stages of the dendritic cells according to the invention are fused as precursor cell, as immature cell or as mature cell with other cells according to per se known methods and optionally further differentiated and/or matured. For treatment or prophylaxis of autoimmune diseases it is preferred to use the loaded cells at an immature stage as set forth in more detail above.

Without intending to be limiting, the invention will be explained in more detail with reference to the following example.

EXAMPLE 1

MUTZ-3, a human CD34+, CD124+, CD116+ cell line for the production of effective DCs by cytokine-induced differentiation of dendritic cells from CD34+ precursor cells, and use of the effective DCs to induce functional T cell subsets for the production of immunotherapeutic agents Materials and Methods Antibodies and Reagents The following was used in the investigations:
PE-labelled monoclonal antibodies (mAbs) against CD40, CD34 and TCR Valpha 24 from Coulter Immunotech (Marseilles, France), against CD1a, CD54, CD83, and CD86 from Pharmingen (San Diego, Calif.), and against CD80 from Becton-Dickinson (San Jose, Calif.).

FITC-labelled mAb against HLA-DR, TCR Vβ 11 and CD14 from Becton-Dickinson, against CD116 (GM-CSF receptor) from Pharmingen.

CD1d expression was assessed using a murine mAb against CD1d (mAb CD1d27) (Spada et al. 1998, J. Exp. Med. 188(8), 1529-1534), followed by a FITC-labelled anti-mouse IgG1 mAb (Pharmingen). The isotype control mouse IgG1 is from Organon Technika-Cappel (Malvern, Pa.), FITC- and PE-labelled Simultest isotype controls from Becton-Dickinson. Langerin expression was detected by means of staining with the mAb DDCM4, followed by a FITC-labelled anti-mouse mAb. Antigen presentation by CD1d was blocked using Ab CD1d51 (Spada et al. 1998, J. Exp. Med. 188(8), 1529-1534).

Cell Cultures

The cytokine-dependent, human myelomonocytic leukemia cell line MUTZ-3 was cultured in MEM-alpha with ribonucleosides and deoxyribonucleosides (Gibco, Paisley, UK), heat-inactivated FCS, penicillin/streptomycin, and 10% conditioned medium of the human bladder carcinoma cell line 5637 (Quentmeier 1996, Leuk. Res. (4), 343-350). The cells were cultured in 6-well plates (Costar, Cambridge, Mass.) at 37° C. and 5% $CO_2$ and passaged twice a week. The cell line THP-1 derived from an acute monocytic leukemia, the cell line KG-1 derived from an acute myelogenic leukemia, the chronic myeloid leukemia line K562, the cell line HL-60 derived from a promyelocytic leukemia, and the macrophage-like histiocytic lymphoma line U937 were obtained from the American Type Culture Collection (ATCC, Rockville, Md.). These cell lines were cultured in IMDM or RPMI-1640 with heat-inactivated FCS, penicillin/streptomycin, 2M L-glutamine and β-mercaptoethanol and passaged twice a week in 80 $cm^2$ tissue culture flasks (Costar).

Generation of Immature (iDC) and Mature DC-Like (mDC) Cells from Leukemia Cell Lines The induction of a DC-like phenotype in leukemia cell lines was accomplished as follows:
The cells were washed and seeded at a cell density of $1 \times 10^5$/ml (in a volume of 3 ml) in 24-well plates and incubated for 7 days with GM-CSF (100 ng/ml, Novartis/Schering-Plough, Arnhem, NL), IL-4 (1000 U/ml CLB) and low-dosed TNFalpha (2.5 ng/ml, CLB, Amsterdam, NL). On day 7 maturation was induced by adding either TNFalpha (75 ng/ml) or LPS (100 ng/ml, Sigma). To produce LC-like cells, the MUTZ-3 cells were cultured for 9 days in GM-CSF and low-dosed TNFα. The cells were then incubated in the presence or absence of TGFβ1 (1 ng/ml, R&D Systems, Abingdon, Oxon UK) and low-dosed TNFα for another 7 days, and the culture medium was renewed on the second day. The immature DCs (iDC) thus obtained were examined for expression of CD1a and langerin.

Flow Cytometry

The cultured cells were washed and resuspended at a cell number of $5 \times 10^4$ to $1 \times 10^5$ in 25 µl of ice-cold FACS buffer (PBS pH 7.5, 0.1% BSA, 0.2% sodium azide). The specific and fluorescence-labelled mAbs or the corresponding isotype controls were added, and the cells were incubated for 30 minutes at 4° C. The cells were washed once and resuspended in 250 µl FACS buffer. The labelled cells were analyzed on a FACStar (Becton-Dickinson) using the CellQuest software.

Allogenic Mixed Lymphocyte Reaction (MLR)

Allogenic, non-adherent PBL were isolated from the peripheral blood of healthy donors by means of gradient centrifugation on Hypaque Lymphoprep (Nycomed, Oslo, Sweden). The cells were seeded in round-bottom microtiter plates at a concentration of $5 \times 10^4$ cells/well and incubated with a dilution series of MUTZ-3 DCs in 200 µl of culture medium for 5 days. The T cell proliferation was determined following a 5 h pulse with $^3$H-thymidine (0.4 µCi/well, Amersham, Aylesbury, UK) (standard methods).

Induction of IL-12/p70 and IL-10 Secretion by Mature MUTZ-3 DCs (MUTZ-3 mDC)

The MUTZ-3 iDCs were washed and seeded in 48-well plates at a cell number of $1 \times 10^5$ in MEM alpha (additives see above). Immature MUTZ-3 DCs (MUTZ-3 iDC) were matured by a treatment with TNFα in combination with either IFNγ (1000 U/ml, Biosource, Camarillo, Calif.) or dexamethasone (1 µmol/l, Sigma) (incubation period 48 h) and subsequent stimulation with irradiated cells of a CD40 ligand-transfected J558 cell line (J558-CD40L, $1 \times 10^5$ cells/well). The concentrations of the secreted cytokines IL-10 and IL-12 (p70 subunit) were determined using ELISA.

Induction of $CD8^+$ T Cells Having Specificity for Influenza Matrix Proteins

MUTZ-3 DCs were infected with 100 pfu/cell of a recombinant adenovirus. This adenovirus encodes the M1 matrix protein gene of the heminfluenza virus (RAd128). For RAd128 infection, the DCs were washed with serum-free medium and incubated with lipofectamine (100 pfu/cell, 1.7 µg/$1 \times 10^8$ pfu). After 2 hours the cells were washed with complete medium and incubated at 37° C. and 5% $CO_2$ overnight. Other MUTZ-3 DCs were loaded with the HLA-A2.1-binding M1-derived peptide $M1_{58-66}$ (50 µg/ml) together with beta-microglobulin (2.5 µg/ml) in serum-free medium at 37° C. overnight. $CD8^+$ T cells (responder) were isolated from HLA-A2+ PBMC using a CD8 T cell MACS isolation kit (Miltenyi Biotec). Antigen-loaded (virus or peptide) MUTZ-3 DCs (stimulator) at a responder/stimulator ratio of 5:1 were used in complete IMDM medium with 10% pooled human serum (CLB) and 5 ng/ml IL-7 (R&D Systems). After one week the T cells were examined for specificity in an IFNγ ELISPOT assay. To this end, irradiated T2 cells were used, loaded either with the M1-derived peptide $M1_{58-66}$ or, as a control, with the HLA-A2.1-binding HPV16-E7-derived peptide ($E7_{11-20}$). The cells were loaded with the peptide (50 μg/ml) and beta-microglobulin (2.5 μg/ml) in serum-free medium at 37° C. overnight.

Induction of CD8+ T Cells Having Specificity for the Melanoma-Associated Antigen MART-1

MUTZ-3 DCs were loaded with the HLA-A2.1-binding MART-1-derived peptide (ELAGIGILTV)(SEQ ID NO: 1) (10μ/ml) for 4 hours at 37° C. in serum-free AIM-V medium (Gibco). CD8+ T cells (responder) were isolated from HLA-A2+PBMC using a CD8 T cell MACS isolation kit (Miltenyi Biotec). MART-1 peptide-loaded MUTZ-3 DCs (stimulator) at a responder/stimulator ratio of 10:1 were used in serum-free AIM-V medium (Gibco). After one week the T cells were examined for specificity in an IFNγ. ELISPOT assay. To this end, irradiated T2 cells were used, loaded either with the HLA-A2.1-binding MART-1 peptide (ELAGIGILTV)(SEQ ID NO: 1) or, as a control, with the HLA-A2.1-binding CEA-derived peptide CEA.78 (IMIGVLVGV)(SEQ ID NO: 2). The cells were loaded with the peptide (1 μg/m1) in serum-free AIM-V medium (Gibco) at 37° C. overnight.

Induction of CD8+ T Cells with Specificity for the Tumor Antigens MUC-1 and Asialoglycophorin by Stimulation with Tumor Cell Lysates The tumor cell lysates were produced either from tumor cell lines or from primary material:
a) Cell lysates from tumor cell lines were produced using 4 cycles of alternating freezing in liquid nitrogen and subsequent thawing according to per se known methods.
b) Cell lysates from solid tumor primary material were produced as follows: Solid tumors were treated using the triple enzyme method, thereby producing single-cell suspensions. This method is well-known to those skilled in the art and is frequently used in various variants in most tumor-pathological/immunological laboratories. Following surgical removal of the tumor, all further steps are carried out under aseptic conditions. The tumor was dissected into pieces about 5 mm³ in size and placed in a vessel with sterile triple enzyme medium (0.1% collagenase, 0.002% deoxyribonuclease, 0.01% hyaluronidase in Hank's buffered saline, HBSS). This was stirred with a magnetic stirrer at room temperature overnight until the solid pieces of tissue had dissolved. Thereafter, the undigested pieces of tissue were removed using a coarse wire grid, and following careful washing in HBSS, the remaining cells were centrifuged with a Ficoll gradient so as to separate monocytes and lymphocytes from the tumor cell suspension. The tumor cells were subsequently lysed using 4 cycles of alternating freezing in liquid nitrogen and subsequent thawing.
MUTZ-3 DC were loaded with a tumor cell lysate in serum-free AIM-V medium (Gibco) at 37° C. overnight. CD8+ T cells (responder) were isolated from HLA-A2+ PBMC using a CD8 T cell MACS isolation kit (Miltenyi Biotec). MUTZ-3 DCs loaded with tumor cell lysate (stimulator) at a responder/stimulator ratio of 10:1 were used in serum-free AIM-V medium (Gibco). After one week the T cells were examined for specificity in an IFNγ ELISPOT assay.

To this end, antigen-loaded MUTZ-3 DCs or peptide-loaded T2 cells were used. The MUTZ-3DCs were loaded with a tumor cell lysate or with asialoglycophorin (protein) in serum-free AIM-V medium (Gibco) at 37° C. overnight. T2 cells were loaded with the HLA-A2.1-binding MUC1 peptide MUC-1.2 (LLLLTVLTV)(SEQ ID NO: 3) (1 μg/ml) in serum-free AIM-V medium (Gibco) for 4 hours.

IFNγ ELISPOT Assay

Multiscreen 96-well filtration plates (Millipore, Molsheim, France) were coated for 3 h at room temperature (RT) or overnight at 4° C. with the mAb 1-D1K (50 μg/ml, 15 μg/ml) in filtrated PBS (Mabtech, Nacka, Sweden). The plates were washed 6 times with serum-free medium and subsequently blocked with filtrated complete medium with 10% FCS for 0.5-1 h at RT. Subsequently, $7.5 \times 10^3$ to $1 \times 10^5$ effector cells/well were incubated with $1 \times 10^4$ target cells at 37° C. and 5% $CO_2$ overnight. The cells were discarded and the plates were washed 6 times with filtrated PBS/0.05% Tween 20. Each well was added with 50 μl mAb 7-B6-1 (1 μg/ml in filtrated PBS), and the plates were allowed to stand for 2-4 h at RT. Following 6 wash steps with filtrated PBS/0.05% Tween 20, 50 μl/well streptavidin-coupled alkaline phosphatase (diluted 1:1000 in PBS) was added, and the plates were incubated for 1-2 h at RT. After 6 additional wash steps with filtrated PBS/0.05% Tween 20, 50 μl of alkaline phosphatase reagent (AP conjugate substrate kit, Biorad, Hercules, Calif.) was added, and this was allowed to stand for 15 min to 1 h, until stain dots had developed. The reaction was quenched with tap water, and the stain dots were counted by two independent persons.

Activation of Tetanus Toxoid (TT)-Specific T Cells

PBMC of donors with partial HLA matching (expressing HLA-DR11, HLA-DQ7, HLA-B44 and HLA-A2) were selected, and the CD4+-PBL were isolated using MiniMACS separation columns (Miltenyi Biotec). Following a 1.5 h adherence to the plastic surface to remove contaminating APC, the cells were incubated with a dilution series of TT-pulsed, immature MUTZ-3 DCs (50 mg/ml, Bilthoven, NL, 12 h in serum-free medium) in 200 μl of medium for 7 d at 37° C. and 5% $CO_2$. T cell proliferation was assessed following a 5 h pulse with ³H-thymidine (0.4 μCi/well, Amersham, Aylesbury, UK) (standard methods).

Presentation of α-Galactosylceramide to vα24+/ vβ11+ NKT cells

Vα24+ T cells, including vα24+/vβ11+ NKT cells, were obtained from PBL by positive selection using autoMACS (Miltenyi Biotec). The purified NKT cells were then co-cultured for 7 days with immature or mature MUTZ-3 DCs pulsed with DMSO (vehicle control) or 100 ng/ml α-galactosylceramide (alpha-GalCer, Pharmaceutical Research Laboratory, Kirin Brewery, Japan), with addition of 10 ng/ml recombinant human IL-7 (R&D Systems) and 10 ng/ml recombinant human IL-15 (R&D Systems), in the presence or absence of blocking anti-CD1d antibodies (CD1d51, 10 μg/ml). The absolute number of NKT cells and the expansion factor were determined using FACS analyses.

Results

Differentiation of MUTZ-3 Cells into Effective DCs of Varying Differentiation Stages and Effector Stages
MUTZ-3 Cells Acquire the Phenotype of Immature DCs Upon Cytokine Administration Initially, we determined the potential of leukemic cell lines of differentiating in the presence of cytokines routinely used to induce DCs. More specifically, we investigated the cell lines treated with cytokines for induced expression of CD1a, a major characteristic of immature dendritic cells (iDC), on the surface of the cells. Three of six tested cell lines (MUTZ-3, KG-1, THP-1) responded to the cytokine cocktail GM-CSF, IL-4 and low-dosed TNFα. The amount of CD1a-positive cells after 7 days in culture was highest in the cell line MUTZ-3 (20%), while the cell lines KG-1 and THP-1 showed 10% and 5% CD1a-positive cells, respectively (Table 1). In the latter two cell lines differentiation was accompanied by marked expression of the DC maturing marker CD83, thus confirming earlier results (Hulette et al. 2001, Arch. Dermatol. Res. 293(3), 147-158; St. Louis et al. 1999, J. Immunol. 162(6), 3237-3248).

KG-1 and THP-1 did not respond to further cytokine stimuli, and also, no further modification of the CD1a/CD83 phenotype was observed. Neither CD1a nor CD83 were detected in the remaining 3 investigated cell lines. All of the tested cell lines were expressing the GM-CSF receptor (CD116), but only the cell line MUTZ-3 was also expressing the IL-4 receptor (CD124). This demonstrates the unique ability of MUTZ-3 cells to become CD1a-positive without simultaneously expressing CD83, i.e., acquiring the iDC phenotype.

MUTZ-3 is a CD34-Positive DC Differentiation Model Derived from Precursor Cells

Figure 2:
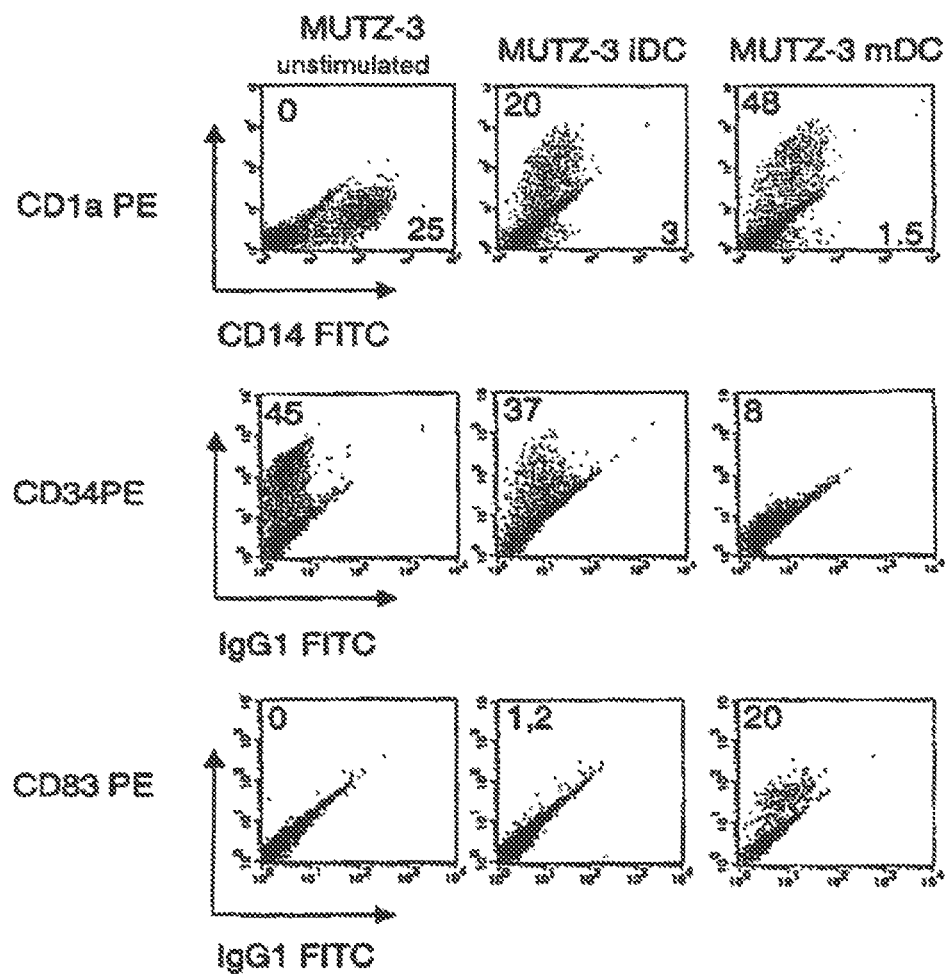
Figure 3:
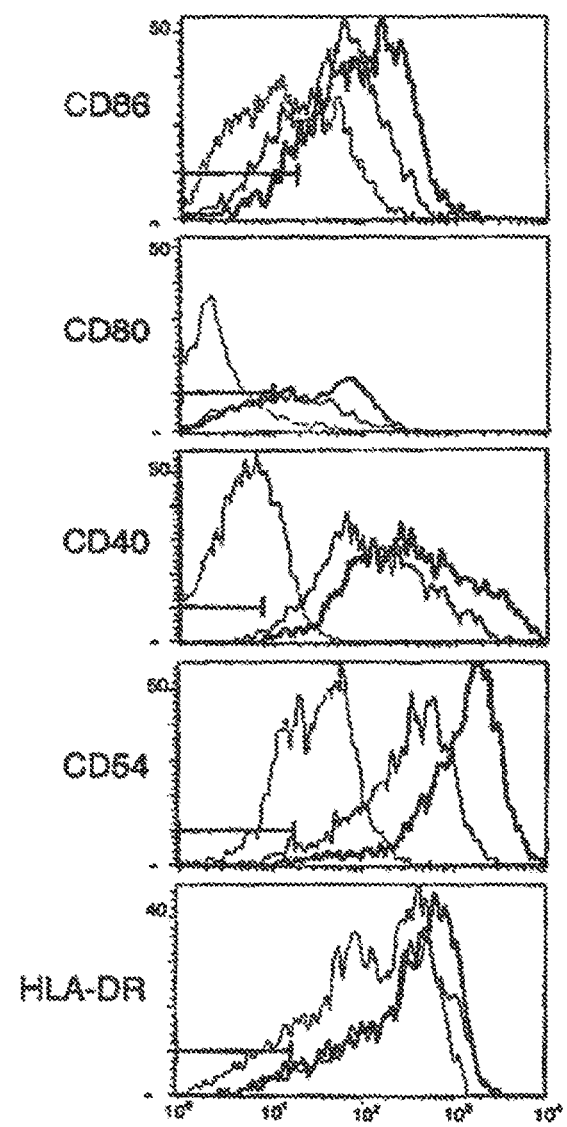

In addition to neo-expression of CD1a, further morphological and phenotypical changes were observed following cytokine stimulation of MUTZ-3 cells. Typically, the MUTZ-3 cells were non-adherent, round or somewhat lobular cells. Subsequent to differentiation, the MUTZ-3 iDCs were no more than loosely adherent, forming lumps of large cells and developing hair-like, cytoplasmatic projections—a morphological characteristic of DCs (FIG. 1a, b). Analysis of the cell surface markers showed sparse expression of CD14, CD86, CD54 and CD40, and strong expression of CD34 and HLA-DR by non-stimulated MUTZ-3 cells (FIGS. 2 and 3). Following induction of CD1a expression on the cell surface, a down-regulated expression of CD14 (monocyte marker) and CD34 (marker of hematopoietic precursor cells) was observed. Expression of the co-stimulatory and adhesion molecules CD80, CD86, CD40, CD54, and HLA-DR was strongly up-regulated on MUTZ-3 iDCs compared to the non-stimulated cell population (FIG. 3). Stimulation of the MUTZ-3 iDCs with TNFα induced expression of the DC maturing marker CD83 with a further increase of CD1a expression and all co-stimulatory molecules. Similar observations were made when the MUTZ-3 iDCs had been matured with LPS, CD40 ligand-transfected J558 cells or polyIC (results not shown). No further proliferation was observed upon addition of cytokines to the MUTZ-3 iDCs or mature DCs (mDC).

Accordingly, MUTZ-3 cells are capable of differentiating into DCs (MUTZ-3 DC) under the influence of GM-CSF, IL-4 and low-dosed TNFα, passing through two different stages of differentiation—an immature (MUTZ-3 iDC) and a mature phenotype (MUTZ-3 mDC).

Such down-regulation of CD34 and CD14 suggests that MUTZ-3 cells represent a population of precursor cells in the differentiation of the CD34-positive stem cells. Differentiation of CD34-positive stem cells gives rise to formation of at least two types of precursor cells which ultimately mature into interstitial and Langerhans cells (LC). To determine whether MUTZ-3 cells would develop into LC-like cells, we have cultured MUTZ-3 cells in the presence or absence of TGFβ1. TGFβ1 is known to induce a LC phenotype in DCs derived from CD34-positive cells (Caux et al. 1997, Blood 90(4), 1458-1470). We observed not only an increase of the amount of CD1-positive MUTZ-3 cells from 20% to 80%, but also strong langerin/CD1a double staining under the influence of TGFβ1, the latter indicating that these cells exhibit specific characteristics of LC cells.

MUTZ-3 DCs Induce Proliferation of Allogenic Lymphocytes

Figure 5:
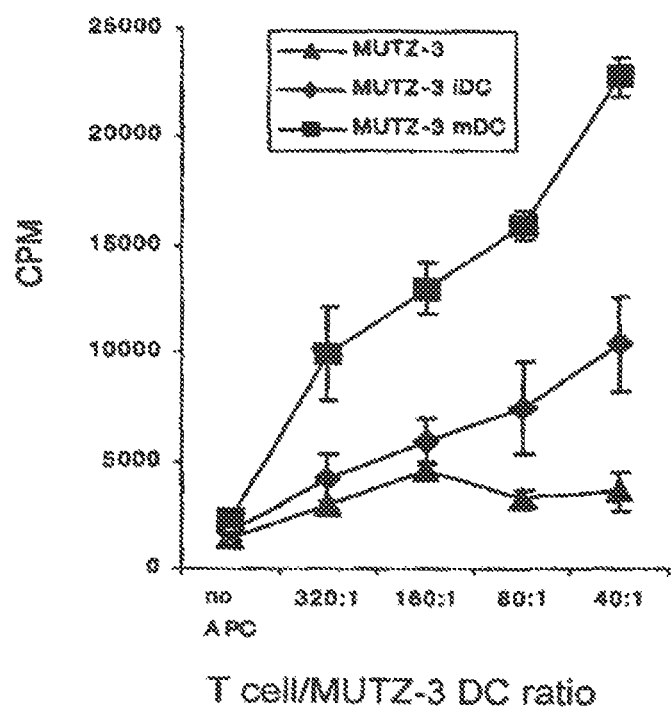

In mixed lymphocyte reactions, MUTZ-3 mDCs were capable of stimulating proliferation of allogenic T cells, and indeed, to a higher degree compared to MUTZ-3 iDCs or non-stimulated MUTZ-3 cells. Incorporation of $^3$H-thymidine (lymphocyte proliferation) increased by 6-10 times compared to non-stimulated MUTZ-3 cells and incorporation of $^3$H-thymidine increased by 2-3 times compared to MUTZ-3 iDCs was measured at a MUTZ-3/PBL ratio of 40:1 (FIG. 5). Such enhanced stimulatory properties of MUTZ-3 mDCs compared to MUTZ-3 iDCs probably reflect the observed increase of expression of the co-stimulatory and adhesion markers CD80, CD86, CD40 and CD54 (as shown in FIG. 3).

Figure 6:
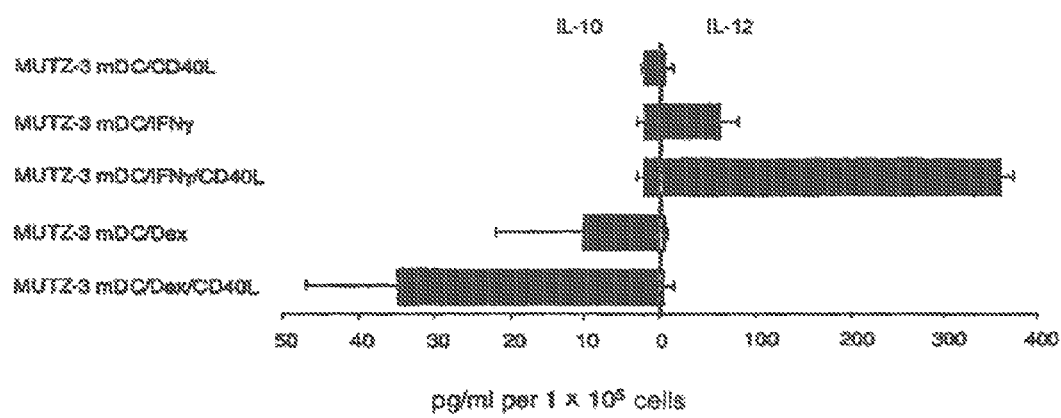

MUTZ-3 DCs Respond to Th-Polarizing Stimuli and Assume a DC1 or DC2 Phenotype During Maturing DCs can secrete IL-12, a potent type 1 T cell-inducing cytokine (Kalinski et al. 1998, J. Immunol. 161(6), 2804-2809). Furthermore, it has been demonstrated that non-preprogrammed iDCs under the influence of particular stimuli assume the capability of secreting mainly IL-12 (DC2 phenotype) or the type 2-inducing cytokine IL-10 (DC2 phenotype) (Vieira et al. 2000, J. Immunol. 164(9), 4507-4512; Langenkamp et al. 2000, Nat. Immunol. 1(4), 311-316). To investigate whether MUTZ-3 iDCs would develop either the DC1 or DC2 phenotype, maturing of the MUTZ-3 iDCs was induced in the presence of IFNγ or dexamethasone. When stimulating MUTZ-3 mDCs (after maturing in the presence of TNFα) in the presence or absence of CD40 ligand-transfected J558 cells, small amounts of IL-10 and IL-12 were produced (FIG. 6). On the other hand, maturing of MUTZ-3 iDCs in the presence of IFNγ gave IL-12 production which, in addition, massively increased when stimulation of the cells by said transfected J558 cells continued (post-maturation). In marked contrast, no IL-12 at all was produced by MUTZ-3 mDCs when maturing thereof was effected in the presence of dexamethasone. However, increased IL-10 production was detected in these cell cultures. These results show that non-preprogrammed MUTZ-3 DCs can be modified into the DC1 or DC2 phenotype under suitable conditions.

MUTZ-3 Cells as Effective DCs Having the Ability to Process and Present Antigens and to Induce an Immune Response One central function of DCs as professional antigen-presenting cells (APC) is their ability to stimulate CD4- and CD8-positive T cells and (as recently shown) present lipids and hydrophobic antigens to NKT cells. We therefore investigated whether MUTZ-3 DCs would be capable of specifically processing and presenting antigens in this way.

MUTZ-3 DCs Activate Influenza-Specific, Cytotoxic T Lymphocytes Via Class I MHC

Molecular typification indicated that MUTZ-3 cells were positive to the HLA antigens HLA-A2, HLA-A3, HLA-B44, HLA-DR10, HLA-DR11, HLA-DR52, HLA-DQ5, and HLA-DQ7. HLA-A2 expression was confirmed by FACS analysis using the monoclonal antibodies MA2.1 and BB 7.1 (results not shown). We then investigated whether MUTZ-3 DCs would be capable of processing and presenting antigens via the HLA-A2 class I molecule. MUTZ3 DCs were loaded with the immunodominant A2-binding M1 heminfluenza (flu) peptide, or the cells were infected with adenoviruses encoding the entire M1 sequence (to test the capability of HLA class I processing). In both cases, T2 cells loaded either with the M1 flu peptide or, as a control, with the HPV-derived E7 peptide were used as stimulator cells in the IFNγ ELISPOT assay for cytotoxic T lymphocytes (CTL) which might have formed during co-culturing of MUTZ-3 DCs and T cells. Unstimulated T cells were added to determine the base line of the flu-specific CTL reaction. No specific CTL response was observed under these conditions (results not shown). An HLA-A2-restricted, flu-specific CTL expansion was detected upon co-culturing of the CTLs with MUTZ-3 DCs which were either loaded with the flu peptide or infected with the M1-encoding adenovirus (FIG. 7a 1,2). These results demonstrate that MUTZ-3 DCs are capable of processing and presenting flu peptides, resulting in a stimulation of flu-specific, class I MHC-restricted CTLs.

MUTZ-3 DCs Induce MART-1-Specific, Cytotoxic T Lymphocytes Via Class I MHC

Figure 9:
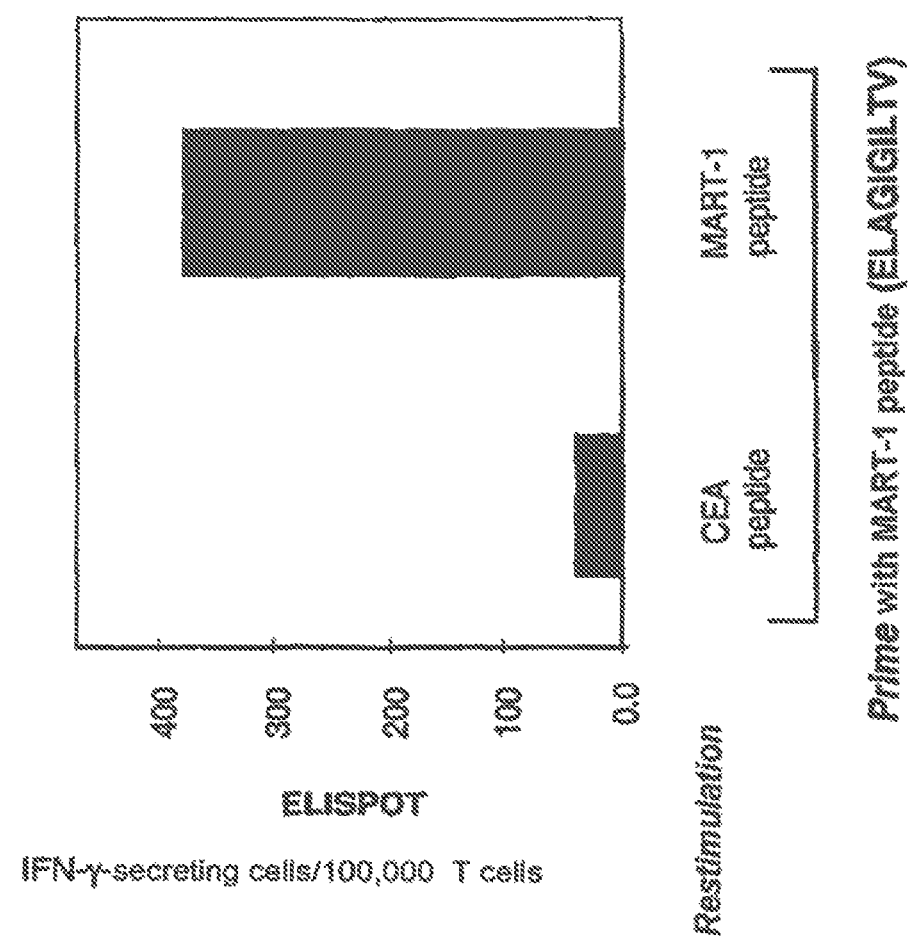

HLA-A2-dependent, MART-1-specific CTL expansion and activation (IFNγ secretion) was detected upon co-culturing of the CTL with MUTZ-3 DCs loaded with the modified MART-1 peptide ELAGIGILTV (SEQ ID NO: 1) (FIG. 9). These results show that MUTZ-3 DCs are capable of sensitizing naive CTLs via class I MHC.

Figure 10:
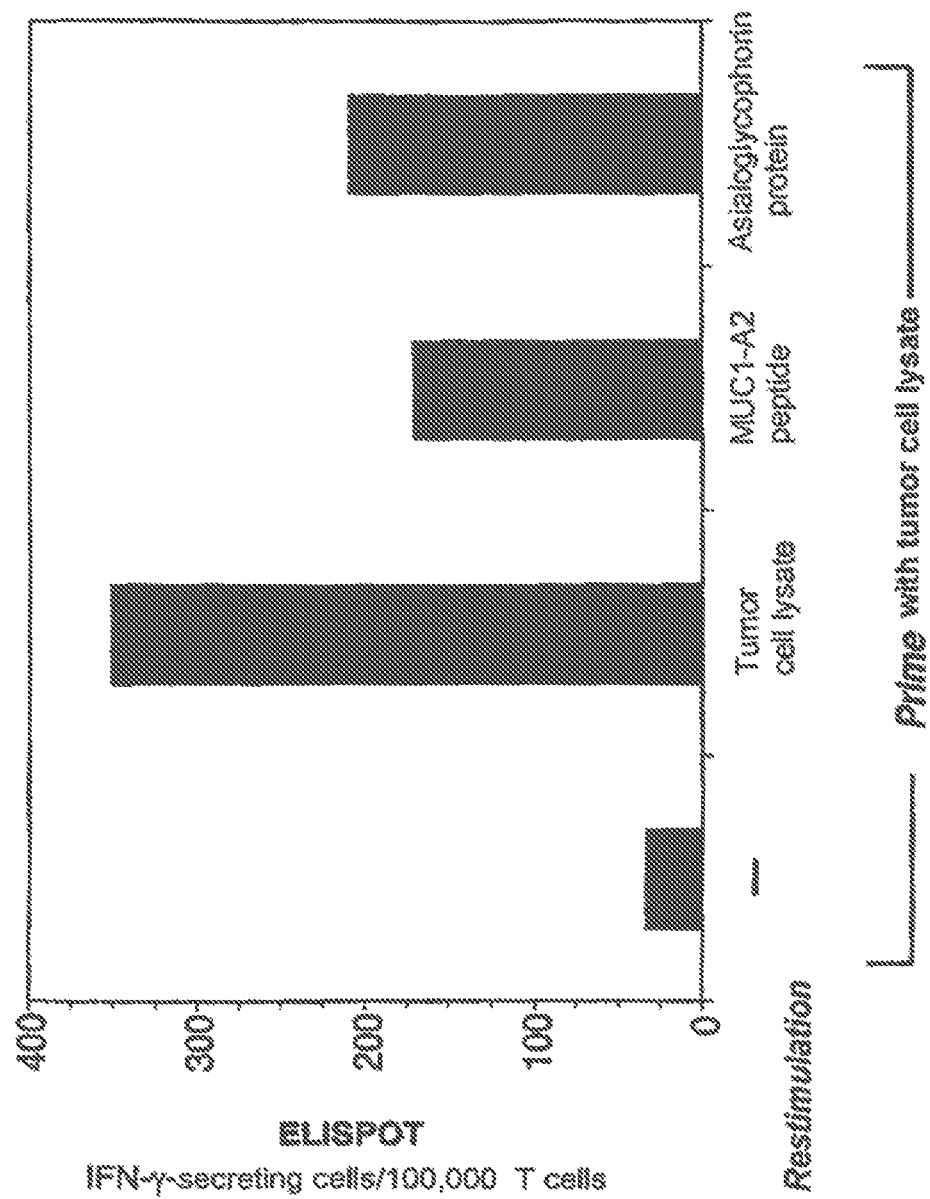

Tumor Cell Lysate-Loaded MUTZ-3 DCs Induce Cytotoxic T Lymphocytes Specific for Different Tumor Antigens HLA-A2-dependent, tumor cell lysate-specific CTL expansion and activation (IFNγ secretion) was detected upon co-culturing of the CTLs with MUTZ-3 DCs loaded with tumor cell lysate (FIG. 10). Activation of these CTLs was also possible by restimulation with the MUC1 peptide LLLLTV-LTV (SEQ ID NO: 3) and by restimulation with the protein asialoglycophorin. These results show that MUTZ-3 DCs are capable of inducing a polyspecific cellular anti-tumor immune response.

Generation of Immature MUTZ-3 (iDC) from Precursor Cells Using GM-CSF, TNFα and Various IL-4 Concentrations or IL-13

MUTZ-3 cells from the current culture were washed twice with PBS and seeded at a cell density of 1×10⁵ cells/ml into a volume of 5 ml of culture medium in a 6-well plate and incubated for 7 days with GM-CSF (1000 U/m, Leukomax, Novartis), low-dosed TNFα (2.5 ng/ml, Peprotech) and various concentrations of IL-4 (between 0.1 U/ml and 1000 U/ml, Peprotech). In another test IL-4 was replaced with IL-13 (100 ng/ml). This concentration corresponds to approximately the 40 fold concentration of the IL-4 concentration used (100 U/ml). Cytokine was added on each second to third day. After 7 days of incubation the cells were characterized by flow cytometry (see FIGS. 11 and 12).

Stimulation of TT-Specific, CD4-Positive T Cells by TT-Pulsed MUTZ-3 iDCs

The capability of peptide processing via the class II MHC pathway was investigated by pulsed loading of MUTZ-3 iDCs with peptides derived from the "common recall" TT antigen and subsequent co-culturing with allogenic CD4-positive T cells partially matching with respect to the HLA type. Strong stimulation of the TT-specific CD4-positive T cells was observed when MUTZ-3 iDCs were loaded with TT peptides in a pulsed fashion, as compared to the vehicle as a control, and the control values were similarly low as in the case of CD4-positive cells alone (FIG. 7b), These results show that MUTZ-3 cells are capable of processing and presenting antigens via the class II MHC pathway.

Glycolipid Presentation by MUTZ-3 DCs to Vα24-Positive/Vβ11-Positive NKT Cells

Figure 8:
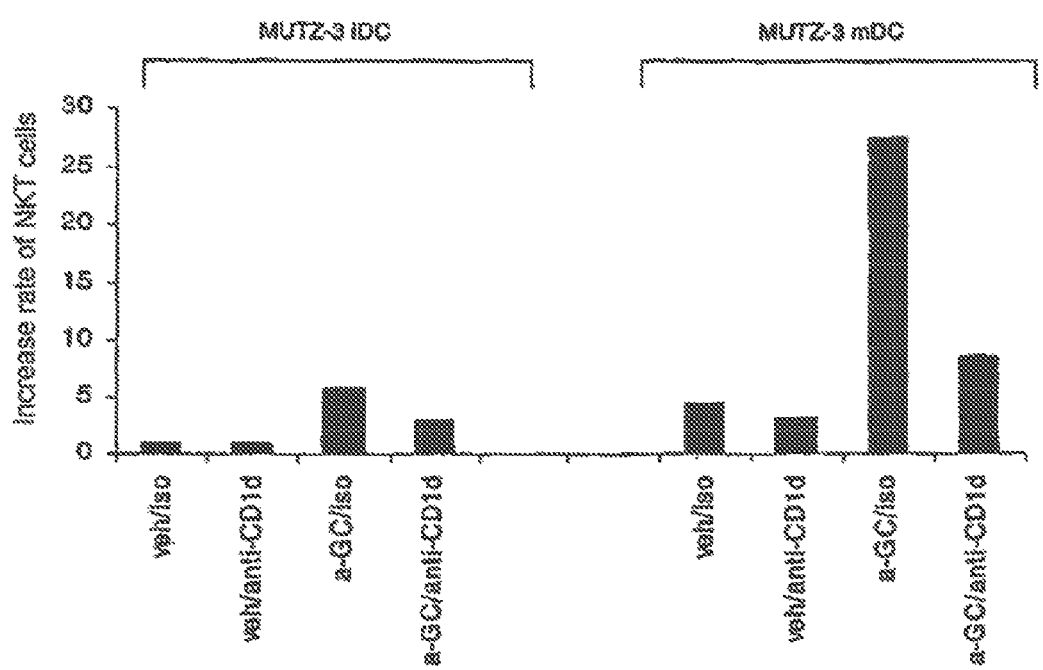

CD1 molecules represent a specialized class of antigen-presenting molecules capable of presenting lipids, glycolipids and hydrophobic peptides. It has been demonstrated that the glycolipid α-GalCer can be presented to Vα24-positive/Vβ11-positive NKT cells (Brossay et al. 1998, J. Exp. Med. 188(8), 1521-1528). To investigate whether MUTZ-3 DCs would be capable of presenting α-GalCer, we initially demonstrated that MUTZ-3 DCs express the CD1d molecule (results not shown). MUTZ-3 iDCs and mDCs were then loaded with α-GalCer or vehicle and co-cultured with purified NKT cells for 7 days in the presence of 10 ng/ml IL-7 and IL-15 (van der Vliet et al. 2001, J. Immunol. Methods 247(1-2), 61-72). α-GalCer-loaded MUTZ-3 mDCs were superior in inducing NKT cells compared to MUTZ-3 iDCs (loaded both with α-GalCer and vehicle) and vehicle-loaded MUTZ-3 mDCs. The termination of antigen presentation by CD1d blocking confirmed the conclusion that MUTZ-3 mDCs are capable of presenting glycolipid antigens via the non-classical antigen-presenting CD1d molecules (FIG. 8).

KEY TO THE DRAWINGS

Table 1. FACS analysis of CD1a and CD83 expression in leukemia cell lines. CD1a and CD83 expression was investigated using flow cytometry following 7 days of incubation with cytokines. With MUTZ-3 cells a neo-expression of CD1a but not of CD83 was observed. Minor induction of CD1a expression with associated CD83 expression was measured for KG-1 and to an even lesser extent also for THP-1 cells. [a] % positive cells represents the total number of cells with positive staining with a particular CD marker within a gated cell population. [b] Cells stained by PE-conjugated anti-CD1a and FITC-conjugated anti-CD83 monoclonal antibodies represent double-positive cells. [c] Cells were stained with FITC-conjugated anti-CD116 monoclonal antibodies. [d] Published in Drexler, H.G. 2001, The Leukemia-Lymphoma Cell Line Facts Book, Academic Press.

FIG. 1. Microscopic images of differentiated MUTZ-3 cells following addition of cytokines. a) Unstimulated MUTZ-3 cells, b) MUTZ-3 iDCs after culturing for 7 days in the presence of GM-CSF, IL-4 and low concentrations of TNFα. The cells are no more than loosely adherent, showing a dendritic morphology (enlarged 40 fold).

FIG. 2. MUTZ-3 DCs show characteristics of immature and mature DCs in the presence of cytokines. The scatter plot representation illustrates the phenotype a) of unstimulated MUTZ-3 cells, b) of immature MUTZ-3 iDCs and c) of TNFα-induced mature MUTZ-3 mDCs. The numbers relate to the percentage of cells positive to the respective CD marker. All cells were stained with PE- or FITC-conjugated, antigen-specific, monoclonal antibodies. The data are derived from one experiment which is representative of five experiments.

FIG. 3. The differentiation of MUTZ-3 cells is associated with the induction of expression of co-stimulatory molecules. FACS analysis indicates induction of the co-stimulatory molecules CD86 and CD40, of adhesion molecule CD54 and class II HLA molecule HLA-DR during MUTZ-3 differentiation; unstimulated MUTZ-3 (dotted line), immature MUTZ-3 iDCs (solid line) and mature MUTZ-3 mDCs (fat solid line). The data are derived from one experiment which is representative of five experiments.

Figure 4:
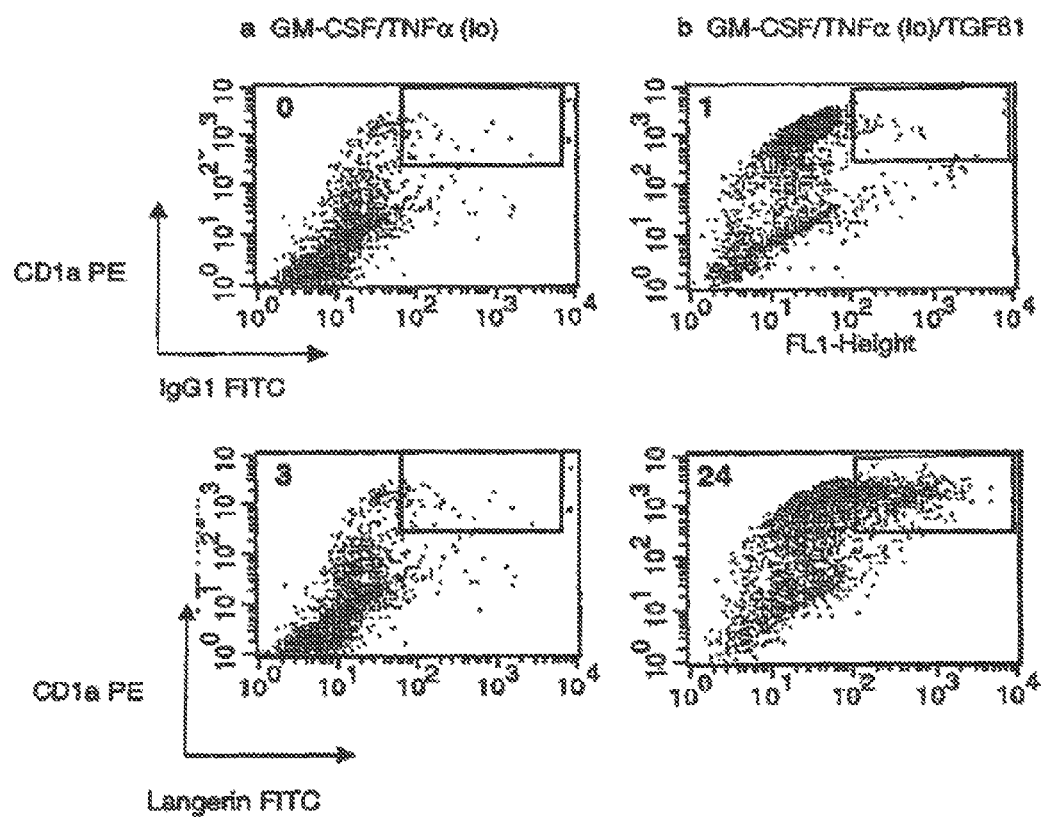

FIG. 4. TGFβ1 induces expression of the LC-associated surface molecule langerin on MUTZ 3 cells. CD34-positive MUTZ 3 cells were initially cultured in the presence of GM-CSF/TNFα and subsequently in the absence of TGFβ1 (panel a) or in the presence of TGFβ1 (panel b). The numbers in the left upper corner relate to the percentage of CD1a/langerin double-positive cells within a gated cell population, or to the percentage of cells stained with an isotypic antibody as a control. The data are derived from one experiment which is representative of three experiments.

FIG. 5. The ability of MUTZ-3 cells to stimulate lymphocytes. Unstimulated MUTZ-3, immature MUTZ-3 iDCs and mature MUTZ-3 mDCs were co-cultured with lymphocytes non-matching in MHC in an allogenic mixed lymphocyte reaction. MUTZ-3 mDCs had a strong stimulatory capacity compared to unstimulated MUTZ-3 cells (by 6.3 higher difference in $^3$H-thymidine incorporation compared to unstimulated cells, and by 2.3 higher difference compared to MUTZ-3 iDCs). The data are derived from one experiment which is representative of four experiments.

FIG. 6. Non-preprogrammed MUTZ-3 iDCs can be modified into the DC1 or DC2 phenotype during maturing under the influence of IFNγ or dexamethasone. MUTZ-3 iDCs cultured in the presence of IFNγ secrete IL-12. No IL-12 production is observed when culturing the cells with dexamethasone. Similarly, the cells do not secrete any IL-10 when treated with IFNγ. IL-12 and IL-10 concentrations were determined using ELISA. The cytokine concentrations are given in pg/ml per $10^5$ cells. The data are representative of four individual experiments.

Figure 7:
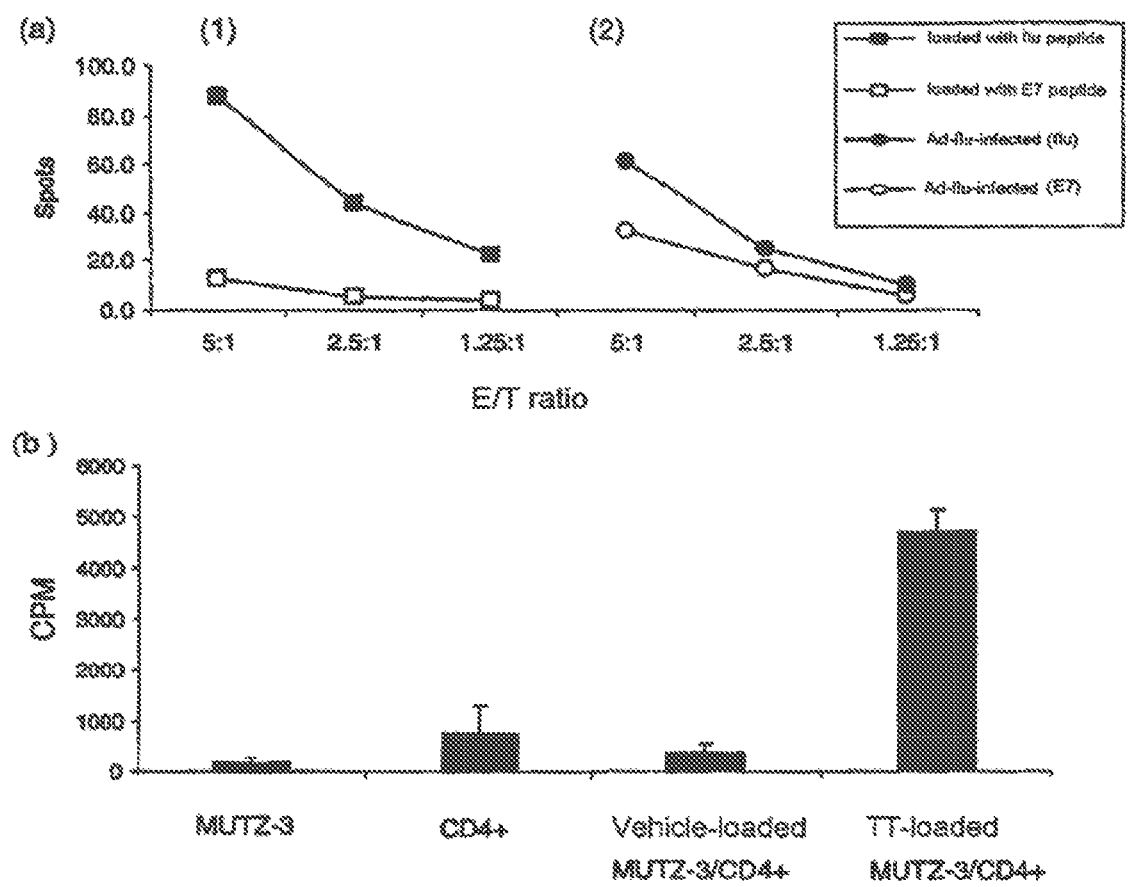

FIG. 7. MUTZ-3 cells have the capability of processing and presenting antigens. (a) Class I MHC presentation. MUTZ-3 iDCs stimulate a flu-specific CTL reaction by presenting the flu peptide restricted to HLA-A2.1. (1) MUTZ-3 DCs were loaded with the HLA-A2.1-binding heminfluenza-derived matrix protein M1$_{58-66}$ and co-cultured with CD8-positive T cells. To detect CTL proliferation the production of IFNγ by the CTLs was measured which were co-cultured with T2 cells as target cells. The T2 cells were either loaded with the M1 flu peptide (black squares) or with the HPV16-derived peptide E7 as control (white squares). (2) MUTZ-3 DCs were infected with recombinant adenoviruses including the M1 matrix protein gene and subsequently co-cultured as described above. Again, CTLs were stimulated with T2 cells loaded either with the M1 flu peptide (black circles) or with the E7 peptide (white circles). The data are derived from one experiment which is representative of three experiments. (b) Class II MHC antigen presentation. MUTZ-3 mDCs process and present peptides derived from the common recall TT antigen and stimulate TT-specific CD4-positive T cells. The data are derived from one experiment which is representative of three experiments.

FIG. 8. Presentation of α-GalCer via CD1d. MUTZ-3 iDCs were loaded either with α-GalCer or with vehicle (DMSO) as control and subsequently cultured for 48 h in the presence or absence of higher-dosed TNFα. Thereafter, mDCs were co-cultured for 9 days in the presence or IL-7 And IL-15 and in the presence or absence of CD1d-blocking antibodies with NKT cells isolated from healthy donors. The results show the relative yield of NKT cells following co-culturing with MUTZ-3 iDCs and mDCs previously loaded with vehicle and α-GalCer, with or without blocking of α-GalCer presentation by the CD1d-blocking antibody. The data are derived from one experiment which is representative of three experiments.

FIG. 9. MUTZ-3 DCs are capable of sensitizing naive CTLs. CTLs were stimulated with MART-1 ELAGIGILTV (SEQ ID NO: 1) peptide-loaded MUTZ-3 DCs (prime) and after one week restimulated overnight with MART-1 ELAGIGILTV (SEQ ID NO: 1) or CEA IMIGVLVGV (SEQ ID NO: 2) peptide-loaded T2 cells. The IFNγ ELISPOT showed strong antigen-specific (MART-1) activation of the CTLs; restimulation with an irrelevant antigen (CEA) gave only sparse activation of the cells.

FIG. 10. MUTZ-3 DCs are capable of inducing a polyspecific anti-tumor CTL response. CTLs were stimulated with tumor cell lysate-loaded MUTZ-3 DCs (prime) and after one week restimulated with tumor cell lysate-loaded MUTZ-3 DCs, with asialoglycophorin-loaded MUTZ-3 DCs, or with MUC1 LLLLTVLTV (SEQ ID NO: 3) peptide-loaded T2 cells. The IFNγ ELISPOT showed strong activation of the CTLs by restimulation of the cells with tumor cell lysate, with the MUC I peptide and with asialoglycophorin.

FIG. 11: MUTZ-3 cells from the current culture were incubated for 7 days with GM-CSF (1000 U/ml), low-dosed TNFα (2.5 ng/ml), and varying concentrations of IL-4 (between 0.1 U/ml and 1000 U/ml). The results show that a reduction of CD124 expression can be observed with increasing IL-4 concentration.

FIG. 12: MUTZ-3 cells from the current culture were incubated for 7 days with GM-CSF (1000 U/ml), low-dosed TNFα (2.5 ng/ml), and in a comparative fashion with IL-4 (100 U/ml) or IL-13 (100 ng/ml). The concentration of IL-13 corresponds to approximately the 40 fold concentration of the IL-4 used. Characterization of the surface molecules by means of flow cytometry shows that comparable expression of surface molecules can be observed in a 7-day incubation with IL-13 instead of IL-4, in addition to GM-CSF and low-dosed TNFα.

In the context with the invention the term "Sensitize" means transferring T lymphocytes into a state of susceptibility to an antigen-specific stimulus.

TABLE 1

FACS analysis of CD1a and CD83 expression on leukemia cell lines. CD1a and CD83 expression was investigated using flow cytometry on day 7 after cytokine addition. CD1a but not CD83 expression can be induced in MUTZ-3 cells. KG-1 and, to a minor extent, TH-1 give CD1a (low) expression in connection with CD83 expression.

| Cell line | % positive cells[a] | | Cytokine receptor expression | |
|---|---|---|---|---|
| | CD1a[b] | CD83[b] | CD116 (GM-CSF receptor)[c] | CD124 (IL-4 receptor)[d] |
| MUTZ-3 | 38 | 0 | + | + |
| KG-1 | 10 | 10 | + | − |
| THP-1 | 5 | 5 | + | − |
| HL-60 | 0 | 0 | + | − |
| U937 | 0 | 0 | + | − |
| K562 | 0 | 0 | + | − |

[a]% positive cells represents the total number of cells with positive staining with a particular CD marker within a gated cell population.
[b]Cells were stained with PE-labelled anti-CD1a and FITC-labelled anti-CD83 monoclonal antibodies; this result represents double-positive cells.
[c]Stained with anti-CD116 FITC-labelled monoclonal antibodies.
[d]By Drexler, H. G. 2001, The Leukemia-Lymphoma Cell Line Facts Book, Academic Press.

The invention claimed is:

1. An isolated MUTZ-3 dendritic cell having a phenotype selected from the group consisting of interstitial dendritic cells, Langerhans dendritic cells, immature dendritic cells and mature dendritic cells, wherein the MUTZ-3 dendritic cell is loaded with at least one antigen.

2. The MUTZ-3 dendritic cell according to claim 1 loaded with a glycolipid.

3. The MUTZ-3 dendritic cell according to claim 1 loaded with a peptide antigen capable of being presented by MHC I molecules.

4. The MUTZ-3 dendritic cell according to claim 1 fused with other cells or cell lines.

5. The MUTZ-3 dendritic cell according to claim 1 loaded with a peptide antigen capable of being presented by MHC II molecules.

6. The MUTZ-3 dendritic cell according to claim 1, wherein the MUTZ-3 cell is CD1d positive.

7. The MUTZ-3 dendritic cell according to claim 1, wherein the MUTZ-3 cell is of DC type 1 or DC type 2.

8. The MUTZ-3 dendritic cell according to claim 1 loaded with cell lysates of tumor cells, tumor cell lines, infected cells or infected cell lines.

9. A kit for the detection of infectious, tumor or autoimmune diseases comprising the MUTZ-3 dendritic cell according to claim 1.

10. A test system for testing immunoactivating, immunoinhibiting or immunmodulating substances or for analyzing the biology of a dendritic cell or dendritic cell line, comprising said MUTZ-3 cell dendritic according to claim 1.

11. A drug comprising said MUTZ-3 dendritic cell according to claim 1, a pharmaceutically tolerable carrier and optionally an additional adjuvant.

12. The drug of claim 11, further comprising an additional adjuvant.

* * * * *

SEQUENCE LISTING

```
<160> NUMBER OF SEQ ID NOS: 3

<210> SEQ ID NO 1
<211> LENGTH: 10
<212> TYPE: PRT
<213> ORGANISM: Homo sapiens

<400> SEQUENCE: 1

Glu Leu Ala Gly Ile Gly Ile Leu Thr Val
1               5                   10

<210> SEQ ID NO 2
<211> LENGTH: 9
<212> TYPE: PRT
<213> ORGANISM: Homo spaiens

<400> SEQUENCE: 2

Ile Met Ile Gly Val Leu Val Gly Val
1               5

<210> SEQ ID NO 3
<211> LENGTH: 9
<212> TYPE: PRT
<213> ORGANISM: Homo sapiens

<400> SEQUENCE: 3

Leu Leu Leu Leu Thr Val Leu Thr Val
1               5
```